US006641568B2

(12) United States Patent
Ashton et al.

(10) Patent No.: US 6,641,568 B2
(45) Date of Patent: Nov. 4, 2003

(54) DISPOSABLE ABSORBENT GARMENT HAVING IMPROVED APPEARANCE AND SUSTAINED FIT

(75) Inventors: Gregory Ashton, Cincinnati, OH (US); Frederick Michael Langdon, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 265 days.

(21) Appl. No.: 09/765,225

(22) Filed: Jan. 18, 2001

(65) Prior Publication Data

US 2002/0095132 A1 Jul. 18, 2002

(51) Int. Cl.$^7$ ................................................ A61F 13/15
(52) U.S. Cl. ......................... 604/385.01; 604/385.03; 604/385.11; 604/385.27; 604/385.29; 604/385.26; 604/385.24; 604/385.23; 604/387; 604/390; 604/392
(58) Field of Search ........................ 604/385.01, 385.03, 604/385.11, 385.27, 385.29, 385.26, 385.24, 585.23, 387, 390, 392

(56) References Cited

U.S. PATENT DOCUMENTS

| | | |
|---|---|---|
| 3,025,856 A | 3/1962 | Burwell et al. |
| 4,315,508 A | 2/1982 | Bolick |
| 4,904,249 A | 2/1990 | Miller et al. |
| 4,909,802 A | 3/1990 | Ahr et al. |
| 4,923,456 A | 5/1990 | Proxmire |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,961,737 A | * 10/1990 | Orlando .................. 604/385.26 |
| 5,246,433 A | 9/1993 | Hasse et al. |
| 5,304,162 A | 4/1994 | Kuen |
| 5,358,500 A | 10/1994 | Lavon et al. |
| 5,649,920 A | 7/1997 | Lavon et al. |
| 5,669,897 A | 9/1997 | Lavon et al. |
| 5,769,838 A | 6/1998 | Buell et al. |
| 5,899,895 A | 5/1999 | Robles et al. |
| 5,899,896 A | 5/1999 | Suprise et al. |
| 6,120,487 A | 9/2000 | Ashton |
| 6,142,983 A | 11/2000 | Suprise et al. |
| 6,174,303 B1 | 1/2001 | Suprise et al. |

FOREIGN PATENT DOCUMENTS

| | | |
|---|---|---|
| EP | 0 323 634 A2 | 7/1989 |
| JP | PTO 99-3266 | 8/1993 |
| WO | WO 91/08725 | 6/1991 |

* cited by examiner

Primary Examiner—John J. Calvert
Assistant Examiner—Angela J Grayson
(74) Attorney, Agent, or Firm—Michael P. Hayden; David M. Weirich; Ken K. Patel

(57) ABSTRACT

Absorbent articles having improved sustained fit on the body, improved appearance through the period of use, and improved comfort for the wearer. The absorbent article has a containment assembly, a waist feature and a diagonal support member feature disposed so as to lie in the diagonal support zone of the wearer's body when the article is worn. The diagonal support member is designed to support the article from the small of the back, over the hip, and to the lower abdomen. The diagonal support member is distinct from the waist feature, which is designed to provide only enough circumferential tension to hold itself in position on the body. The absorbent article has a garment-like high-waisted appearance, gentle tension around the waist to avoid discomfort and/or pressure marking, good leakage protection, good sustained fit, and easy application and removal.

43 Claims, 15 Drawing Sheets

DISPOSABLE ABSORBENT GARMENT HAVING IMPROVED APPEARANCE AND SUSTAINED FIT

FIELD OF THE INVENTION

The present invention relates to absorbent articles such as diapers, incontinence briefs, training pants, diaper holders and liners, sanitary hygiene garments, and the like. More particularly, the present invention relates to absorbent articles providing improved appearance and/or improved sustained dynamic fit during use.

BACKGROUND OF THE INVENTION

Absorbent articles such as diapers and training pants tend to slide downward on the body of the wearer, especially when loaded with excreta. This relative movement creates gaps between the article and the body, through which leakage can occur. It also creates wrinkles that detract from the desirable garment-like appearance of the article. The designs of absorbent articles typically include features intended to sustain the proper fit of the absorbent article on the body. However, these features known in the art are only partially effective in sustaining fit, tend to cause discomfort for the wearer, and/or make application and/or removal of the article difficult.

For example, the designs of many absorbent articles depend upon a waist feature to counteract the downward force of gravity by restricting the size of the waist opening. However, the wearer of an absorbent article often has a protuberant abdomen, rather than a well-defined waist. The waist edge of the absorbent article will naturally slide downward from its initial position on the protuberant abdomen to the area of a diagonal support zone lying across the small of the back, over the hip joints, and across the lower abdomen. Some designs use friction to resist relative movement at the waist, with the waist feature providing the required normal force by generating circumferential tension around the body. However, when the abdomen becomes larger than its initial size, the waist feature naturally seeks a position of lower tension off the expanded abdomen. Because the article is restrained from moving upward, the waist feature typically moves downward toward the diagonal support zone in this situation. When the abdomen becomes smaller, the article also tends to move downward, because the tension and the frictional resistance diminish. When a waist feature is designed to generate a high force in an attempt to minimize downward movement, the greater force often causes discomfort to the wearer and/or creates pressure marks on the body. The greater force may also tend to move the article downward, and/or make spreading of the waist opening for application and/or removal of the article difficult.

The designs of some absorbent articles include side panels or waist belts which supplement or replace waist features. Examples of such absorbent articles are described in U.S. Pat. No. 6,120,487 issued Sep. 19, 2000, and U.S. Pat. No. 5,899,895 issued May 4, 1999, which are hereby incorporated herein by reference. These features tend to exert excessive force on areas of the body where they are stretched a greater amount relative to other areas, causing discomfort and/or pressure marks on the body. Also, when the elastic components move toward positions where they are stretched a lesser amount, they tend to bunch and/or slide together such that the forces they exert are concentrated on a smaller area of the body, often causing discomfort and/or pressure marking. Some side panels also expand and contract to maintain contact of the article about the legs of the wearer. In the designs of some such side panels, an elastic component is angled with respect to the main waist feature and has one end located on or near the front edge of the waist opening and another end located on or near the back edge of the leg opening. Such an elastic component which is angled downward toward the back exerts a downward force on the front portion of the article, adding to the other forces described above in tending to move the absorbent article downward and away from the position in which it is initially fit onto the body.

In some designs of absorbent articles, the front edge of the waist opening curves downward to fit below or at the abdominal crease. Examples of such absorbent articles are described in U.S. Pat. No. 5,358,500 issued Oct. 25, 1994, which is hereby incorporated herein by reference. Because they are initially fit in the area of the diagonal support zone, these low-cut articles often have better sustained fit than articles having higher waist openings. However, several desirable properties are relinquished in exchange for this improvement in sustained fit. The risk of leakage from such a low-cut absorbent article is generally greater, especially for a male wearer, whose urinary stream is often directed toward the waist. The appearance of such a low-cut article differs appreciably from that of a durable garment or of an absorbent article having the garment-like appearance desired by many users. Such a low-cut absorbent article has less area over which to distribute the absorbent core and thus an absorbent core of a given volume may generally be of greater thickness in such a low-cut article.

Thus, it would be beneficial to provide an absorbent article designed to sustain the proper fit of the article on the body. It would also be beneficial to provide an absorbent article having improved appearance throughout its period of use. It would be of further benefit to provide an absorbent article having a reduced possibility of leakage. Additionally, it would be of benefit to provide an absorbent article having easy application and/or removal.

SUMMARY OF THE INVENTION

The present invention provides absorbent articles, such as diapers, incontinence briefs, pull-on diapers, training pants, feminine hygiene garments, and the like, which may provide some or all of the benefits of improved sustained fit on the body, improved appearance through the period of use, and improved comfort for the wearer.

Such an absorbent article is intended to be fit about a wearer's body to contain excreta and/or bodily exudates. The absorbent article has a containment assembly having a front waist region, a back waist region opposed to the front waist region, a crotch region disposed between the front waist region and the back waist region, a front end edge, a back end edge, a topsheet, a backsheet, and an absorbent core disposed at least partially between the topsheet and the backsheet. The absorbent article also has at least one waist feature disposed substantially adjacent either the front end edge or the back end edge. Furthermore, the absorbent article has at least one diagonal support member designed to support the absorbent article on the body substantially in the diagonal support zone which lies across the small of the back over the hip joints and across the lower abdomen. When the absorbent article is worn, a first end of the diagonal support member preferably lies substantially adjacent the back waist region of the absorbent article and a second end of the diagonal support member preferably lies substantially adjacent the lower abdomen of the wearer's body.

The diagonal support member preferably bears the major portion of the weight of the absorbent article and resists downward force caused by changes in bodily shape or dimension. As a result, the waist feature may be subjected to only minimal downward force. Therefore, the waist feature may be designed to provide only enough circumferential tension to hold itself in position on the body and thus avoid causing discomfort for the wearer and/or pressure marking on the wearer's body.

The absorbent article may thus provide a garment-like high-waisted appearance, gentle tension around the waist to avoid discomfort and/or pressure marking, good leakage protection, good sustained fit, and easy application and removal.

BRIEF DESCRIPTION OF THE DRAWINGS

While the specification concludes with claims particularly pointing out and distinctly claiming the subject matter which is regarded as forming the present invention, it is believed that the invention will be understood from the following description which is provided in conjunction with the accompanying drawings, in which like designations are used to designate substantially identical elements, and in which:

DETAILED DESCRIPTION OF THE INVENTION

The term "absorbent article" herein refers to a device which absorbs and contains excreta and/or bodily exudates and, more specifically, refers to a device which is placed against or in proximity to the body of the wearer to absorb and contain the excreta and/or exudates discharged from the body. The term "unitary absorbent article" herein refers to an absorbent article which is formed of separate parts united together to form a coordinated entity so that separate manipulative parts, such as a separate holder and/or liner, are not required. The term "disposable article" herein refers to an article which generally is not intended to be restored or reused, but is instead intended to be discarded after a single use. The term "diaper" refers to an absorbent article generally worn by infants and incontinent persons about the lower torso. The present invention is applicable to absorbent articles such as diapers, pull-on diapers, training pants, incontinence briefs, incontinence undergarments, absorbent inserts, diaper holders and liners, feminine hygiene garments, and the like.

Figure 1:
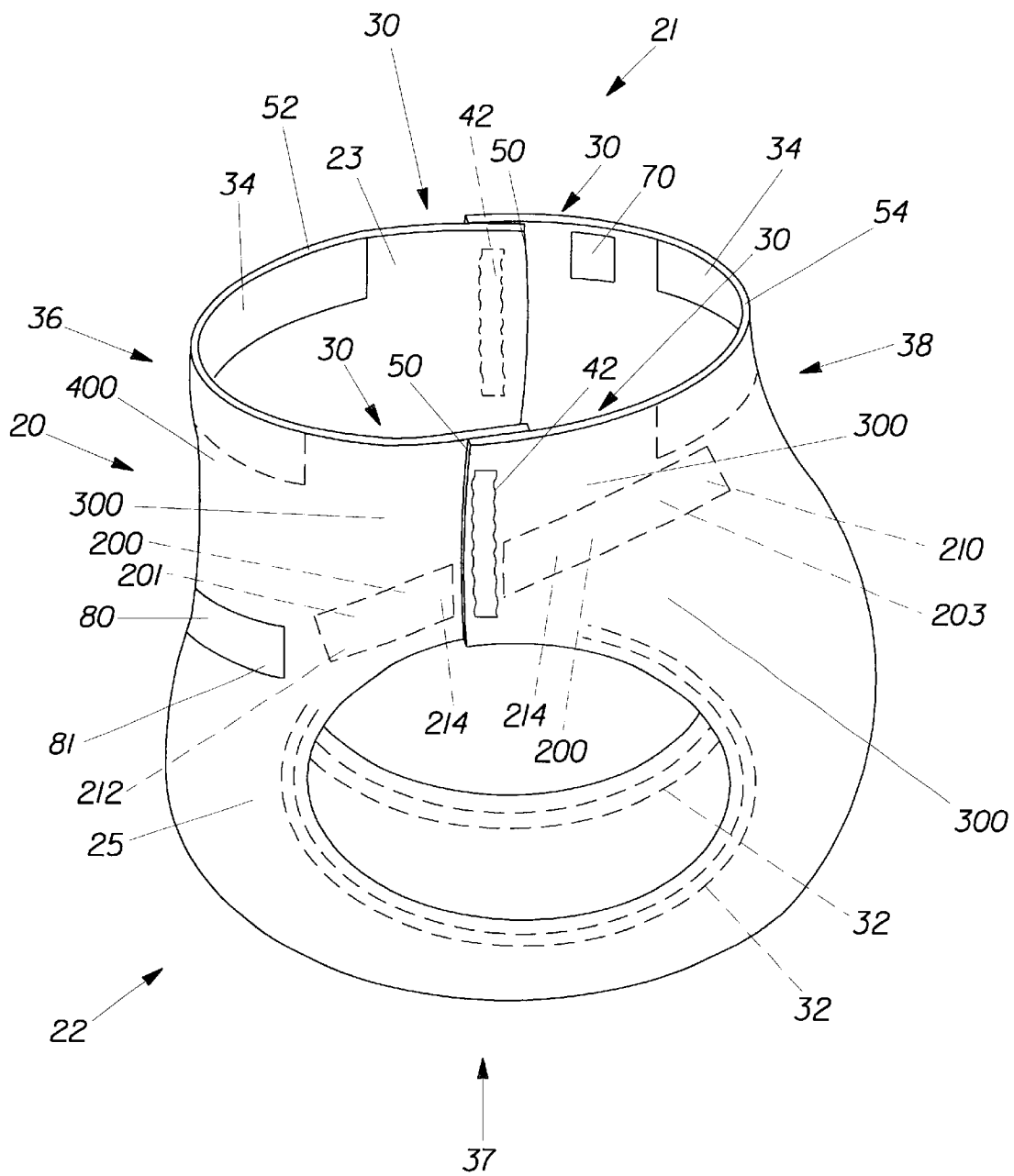
FIG. 1 is a side perspective view of a pre-closed absorbent article embodiment of the present invention.
Figure 2:
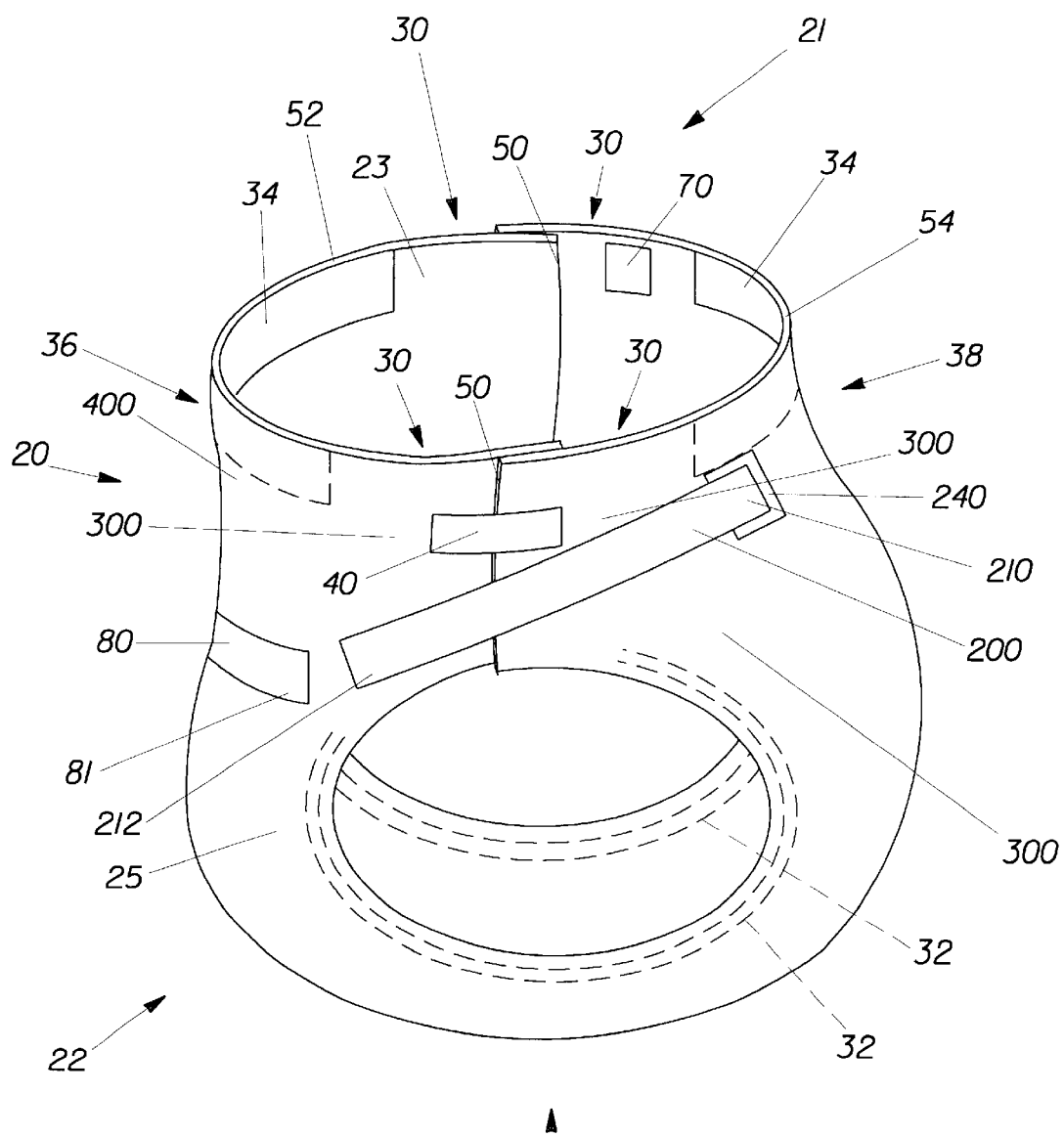
FIG. 2 is a side perspective view of a non-pre-closed absorbent article embodiment of the present invention in assembled form.
Figure 3:
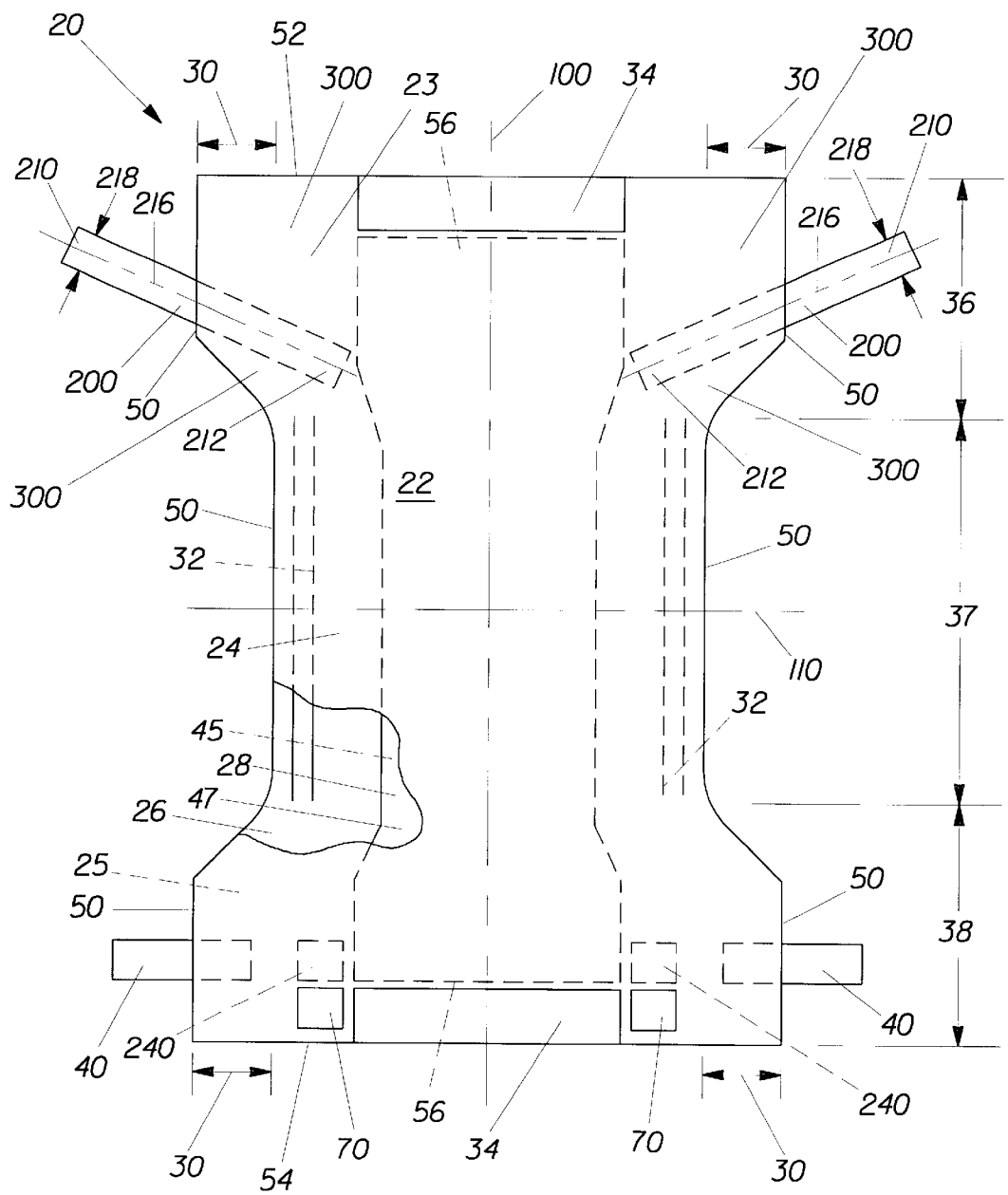
FIG. 3 is a simplified plan view of the article in FIG. 2, laid out flat with the inner surface facing the viewer, showing various sections and structural elements and having portions cut away to reveal underlying structure.
Figure 4:
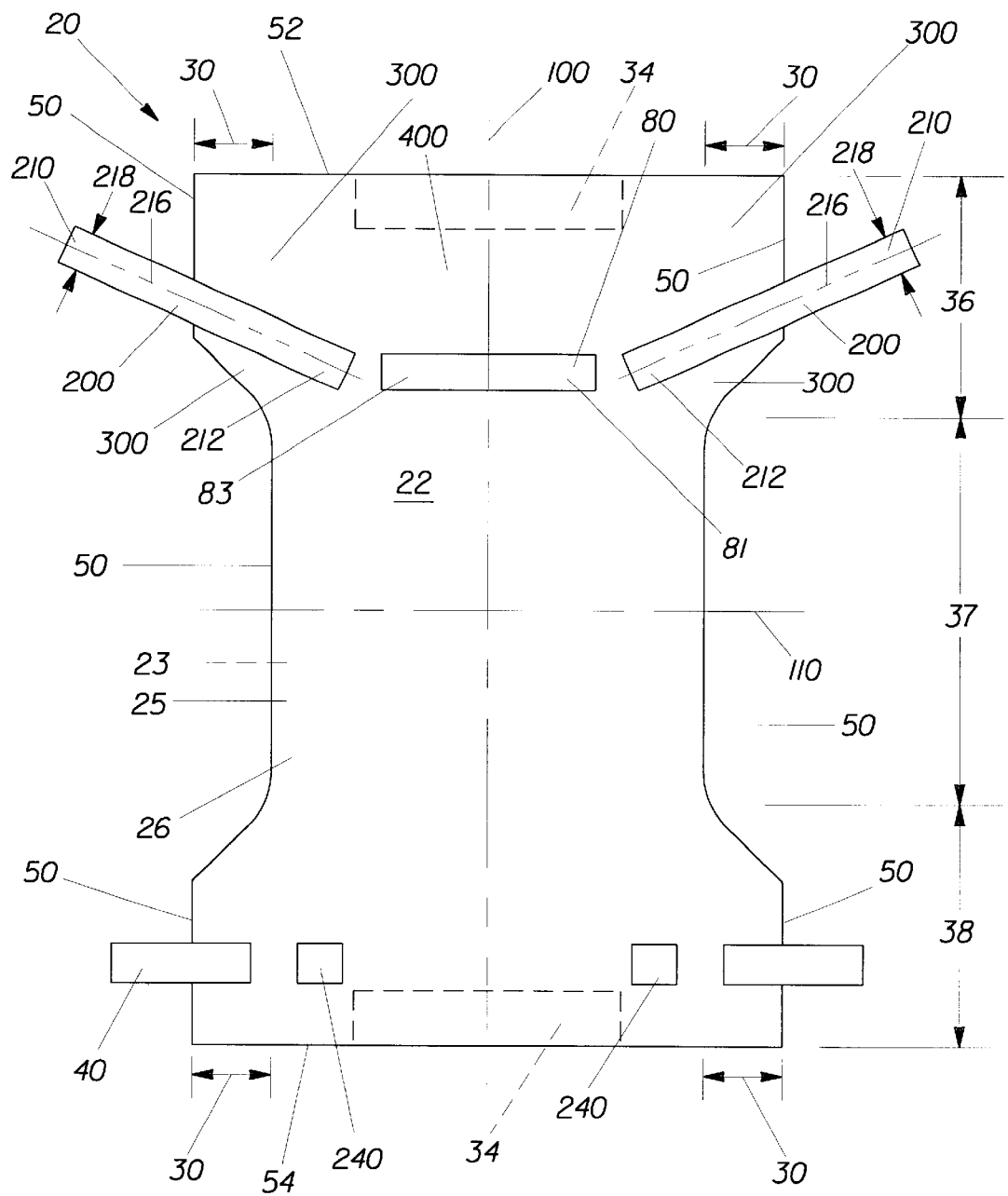
FIG. 4 is another simplified plan view of the article in FIG. 2, laid out flat with the outer surface facing the viewer and showing various sections and structural elements.

An exemplary embodiment of an absorbent article of the present invention is the unitary disposable absorbent article, diaper 20, shown in FIG. 1 in pre-closed form suitable for use as a pull-on diaper or training pant. The diaper 20 in conventional non-pre-closed form, is shown in FIG. 2. The diaper 20 of FIG. 2 is also shown in a flat and uncontracted state in FIG. 3 with the portion of the diaper 20 which faces the wearer oriented toward the viewer, and in FIG. 4 with the portion of the diaper 20 which faces away from the wearer oriented toward the viewer. In some of the drawings, portions of the structure have been cut away to more clearly show the construction of the exemplary absorbent articles. Elements of the diaper 20 which are substantially identical in different embodiments and/or in different drawings are designated herein by the same numerals.

The diaper 20 preferably includes a containment assembly 22, a waist feature 34, and a diagonal support member 200. The diaper 20 has a front waist region 36, a back waist region 38 opposed to the front waist region 36, and a crotch region 37 located between the front waist region 36 and the back waist region 38. The periphery of the diaper 20 is defined by the outer edges of the diaper 20 in which side edges 50 lie generally parallel to the longitudinal centerline 100 and the front end edge 52 and back end edge 54 lie generally parallel to the lateral centerline 110 of the diaper 20 and extend between the side edges 50.

The containment assembly 22 of the diaper 20 preferably includes a liquid pervious topsheet 24, a liquid impervious backsheet 26, and an absorbent core 28 which is preferably positioned between at least a portion of the topsheet 24 and the backsheet 26. The containment assembly 22 constitutes the main structure of the diaper with other features added to form the composite diaper structure. The containment assembly 22 has an inner surface 23 which generally is in contact with the body or in close proximity to the body when the article is worn. The containment assembly 22 also has an outer surface 25 opposed to the inner surface 23 and which generally is in contact with or in close proximity to any garment being worn. The topsheet 24, the backsheet 26, and the absorbent core 28 may be assembled in a variety of configurations well known in the art. Exemplary containment assembly structures are described in U.S. Pat. No. 5,899,895 issued May 4, 1999 and U.S. Pat. No. 6,120,487 issued Sep. 19, 2000, which are hereby incorporated herein by reference.

The backsheet 26 is generally that portion of the diaper 20 which is disposed adjacent the garment-facing surface 45 of the absorbent core 28 and which prevents the excreta and/or exudates contained therein from soiling articles which may contact the diaper 20, such as bedsheets and undergarments. The term "disposed" refers herein to the arrangement of an element in a particular physical relationship to other elements of the absorbent article. In preferred embodiments, the backsheet 26 is substantially impervious to liquid and may comprise any suitable thin plastic film known in the art, including a breathable film. Exemplars of suitable backsheet films include those manufactured by Tredegar Industries, Inc., or Terre Haute, Ind., USA, and sold under the trade names X15306, X10962, and X10964.

The backsheet 26 may be joined to the topsheet 24, the absorbent core 28 or any other element of the diaper 20 by any attachment means known in the art. The term "joined" refers herein to the attachment together of elements of the absorbent article, either by direct affixment of a first element to a second element or by affixment of the first element to an intermediate element which is affixed to the second element. For example, the attachment means may include a uniform continuous layer of adhesive, a patterned layer of adhesive, or an array of separate lines, spirals, or spots of adhesive. Exemplars of suitable adhesives include those manufactured by H.B. Fuller Company of St. Paul, Minn., USA and marketed as HL-1620 and HL-1358-XZP. Alternatively, the attachment means may comprise heat bonds, pressure bonds, ultrasonic bonds, dynamic mechanical bonds, or any other suitable attachment means or combinations of attachment means known in the art.

The topsheet 24 is preferably disposed adjacent the body-facing surface 47 of the absorbent core 28 and may be joined to the absorbent core 28 and/or to the backsheet 26 by any attachment means known in the art. The topsheet 24 is preferably compliant, soft-feeling, and non-irritating to the wearer's skin. Preferably, at least a portion of the topsheet 24 is liquid pervious, permitting liquids to readily penetrate through its thickness. A suitable topsheet may be manufactured from a wide range of materials known in the art, such as porous foams, reticulated foams, apertured plastic films, or woven or nonwoven materials of natural fibers such as wood or cotton fibers, or synthetic fibers such as polyester or polypropylene fibers, or a combination of natural and synthetic fibers. If the topsheet 24 includes fibers, the fibers may be spunbond, carded, wet-laid, meltblown, hydroentangled, or otherwise processed as is known in the art. An exemplar of a suitable topsheet non-woven material is manufactured by Veratec, Inc., a division of International Paper Company of Walpole, Mass., USA, and is designated P-8.

The absorbent core 28 may comprise any absorbent material which is generally compressible, conformable, non-irritating to the wearer's skin, and capable of absorbing and retaining liquids such as urine and other bodily exudates. The absorbent core 28 may be manufactured in a wide variety of sizes and shapes, for example, rectangular, hourglass, "T"-shaped, asymmetric, etc. The absorbent core 28 may include any of a wide variety of liquid-absorbent materials commonly used in disposable diapers and other absorbent articles, such as comminuted wood pulp, which is generally referred to as airfelt, cellulose wadding, melt-blown polymers, chemically stiffened, modified, or crosslinked cellulosic fibers, tissue, absorbent foams including those prepared from polymerization of a high internal phase emulsion, superabsorbent polymers, absorbent gelling materials, or any other known absorbent material or combinations of materials. Exemplary absorbent core structures are described in U.S. Pat. No. 4,610,678 issued Sep. 9, 1986 and U.S. Pat. No. 5,260,345 issued Nov. 9, 1993, both of which are hereby incorporated herein by reference.

The diaper 20 of the present invention includes at least one waist feature 34 as shown, for example, in FIG. 1 and other figures. The waist feature 34 preferably is disposed at least longitudinally outwardly from at least one of the waist edges 56 of the absorbent core 28 and generally forms at least a portion of the front end edge 52 and/or the back end edge 54 of the diaper 20. The waist feature 34 may comprise one or more separate elements affixed to the diaper 20 and/or may comprise an extension of another element of the diaper 20, such as the backsheet 26 and/or the topsheet 24. The waist feature 34 may be substantially inelastic or may be at least laterally elastically extensible to dynamically fit at the wearer's waist. The terms "elastic" and "elastically extensible" refer herein to the property of a material and/or an element of the diaper 20 whereby the material and/or the element can be elongated to a practical extent upon the application of tension and will substantially return to its original length or near its original length after the tension is released. Disposable diapers often have a waist feature 34 disposed in both the front waist region 36 and the back waist region 38. The waist feature 34 may be constructed in any of several different configurations known in the art. Exemplary waist feature constructions include those described in U.S. Pat. No. 4,515,595 issued May 7, 1985 and U.S. Pat. No. 5,221,274 issued Jun. 22, 1993, both of which are hereby incorporated herein by reference.

In the diaper 20 of the present invention, the waist feature 34 preferably provides generally only minimal lateral force, that is, lateral force sufficient only to hold the front waist region 36 and the back waist region 38 substantially in contact with the body. This level of lateral force is adequate because the waist feature 34 preferably is subjected to only minimal downward force, due to the diaper 20 being configured such that the diagonal support member 200 resists downward force. As a result, the waist feature 34 generally remains in position substantially where it is initially fit, with the front end edge 52 remaining near the navel 11 of the wearer's body. The term "downward" refers herein to a direction generally from the head toward the feet on the body of a wearer in all bodily positions and postures.

In some embodiments, the diaper 20 preferably includes a fastening system 40 as shown, for example, in FIG. 1 and other figures. The fastening system 40 preferably maintains the front waist region 36 and the back waist region 38 in a hoop configuration such that lateral force exerted by the waist feature 34 and/or another element of the diaper 20 contributes to circumferential tension which is aligned substantially parallel to the front end edge 52 and back end edge 54, which form the waist opening 21 when the diaper 20 is worn. The fastening system 40 preferably is disposed at least partially adjacent at least a portion of the side edges 50 of the front waist region 36 and/or the back waist region 38. In general, the fastening system 40 may comprise any known fastening means. For example, the fastening system 40 may comprise surface fasteners such as tape tabs, hook and loop fastening components, and/or hermaphroditic fastening components. Furthermore, the fastening system 40 may include buttons, hooks, buckles, and/or other fastening components. In some embodiments, the fastening system 40 may include refastenable fastening means that allow the diaper 20 to be opened and re-fastened, for ease of fitting on and removal from the body of the wearer and for adjustment while the diaper 20 is worn. An exemplar of a suitable fastening system 40 is described in U.S. Pat. No. 5,242,436 issued Sep. 7, 1993, which is hereby incorporated herein by reference.

Figure 8:
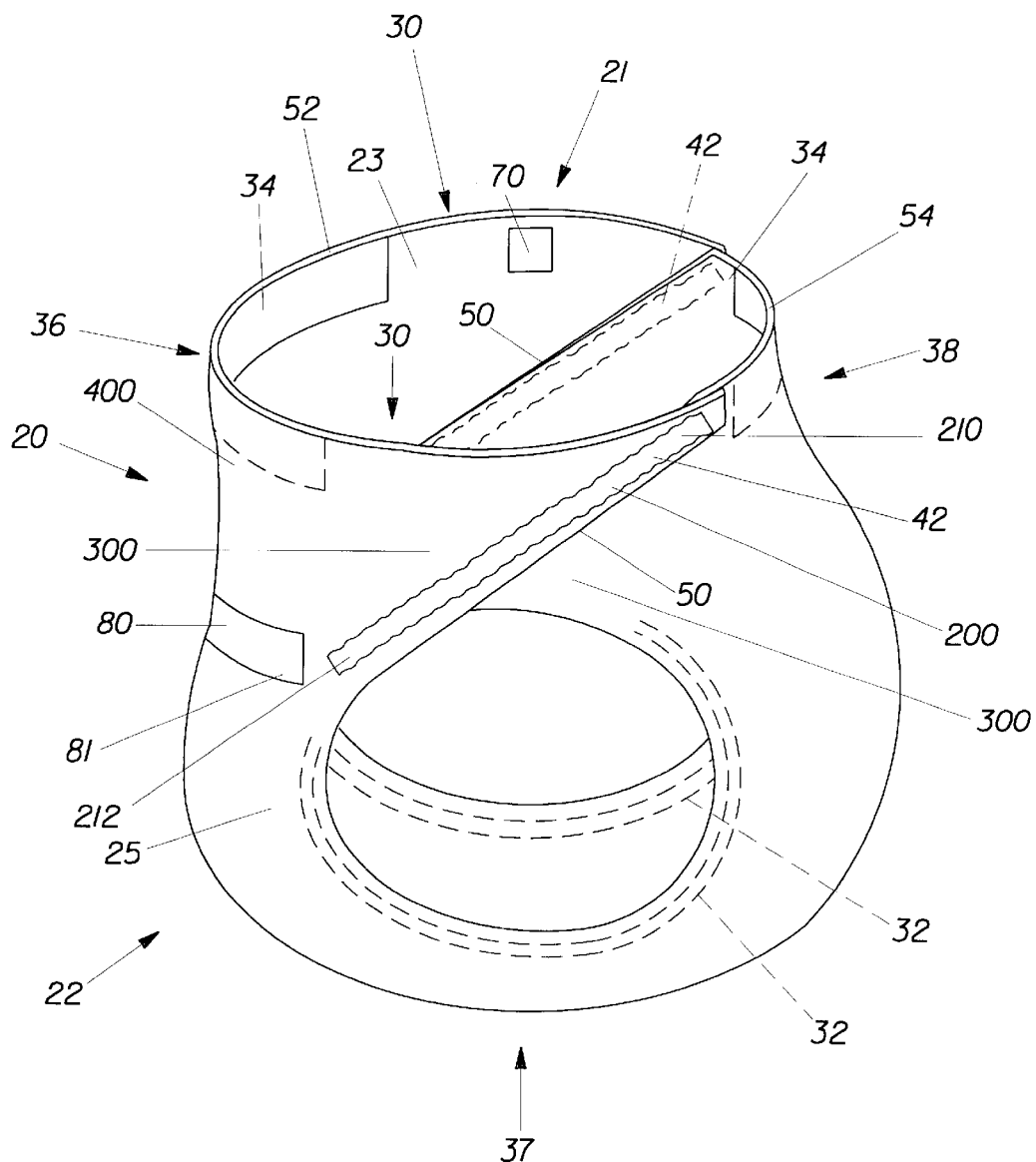
FIG. 8 is a side perspective view of an alternative pre-closed embodiment of the absorbent article of the present invention.

In some embodiments, the diaper 20 may be provided in a pre-closed form as shown, for example, in FIG. 1 and FIG. 8, suitable for use as a pull-on diaper, training pant, or the like. The term "pre-closed" refers herein to a form of an article in which the article is assembled and ready for use. The pre-closed diaper 20 may have its opposing side edges 50 in the front waist region 36 and the back waist region 38 joined by seams or welds 42, as shown in FIG. 1. The seams or welds 42 may be bonded by any suitable bonding means known in the art which is appropriate for the specific materials employed. For example, suitable bonding means may include ultrasonic sealing, heat sealing, pressure bonding, adhesive bonding, sewing, autogenous bonding, and the like. The seams or welds 42 may be permanent, that is, they may be bonded such that separation of the joined opposing side edges 50 requires the rupture or other destructive manipulation of the bonded materials. A pre-closed diaper 20 may alternatively have its opposing side edges 50 fastened together by any suitable fastening means, including those described above for the fastening system 40. In some embodiments, the fastening system 40 of a pre-closed diaper 20 may have refastenable fastening means that allow the diaper to be opened and re-fastened, for ease of fitting on and removal from the body of the wearer and for adjustment while the diaper 20 is worn. In an embodiment in which a pre-closed diaper 20 has a fastening system 40, the fastening system 40 preferably is disposed at least partially adjacent at least a portion of the side edges 50 of the front waist region 36 and/or the back waist region 38.

The diaper 20 may also include at least one high friction retention zone 70 as shown, for example, in FIG. 1 and other figures. The high friction retention zone 70 preferably is disposed at least partially on the inner surface 23 of the containment assembly 22 in either the front waist region 36 or the back waist region 38. A function of the high friction retention zone 70 is to resist movement of the diaper 20 relative to the surface of the wearer's body and in particular to resist downward movement of the diaper 20. The high friction retention zone 70 preferably has a coefficient of static friction to the body which is at least about twice the coefficient of static friction to the body of the material forming the inner surface 23 of the containment assembly 22. The high friction retention zone 70 may comprise an area of a coating and/or a patch of a suitable material. Examples of suitable coating materials include polymeric materials, rubber-based materials, and/or latex or hot-melt materials. Suitable patch materials are typically thin and flexible and can be firmly affixed to the inner surface 23 of the containment assembly 22. Examples of suitable patch materials include polymeric films, fibrous sheets, and/or scrims. Examples of a high friction retention zone 70 are described in co-pending and commonly assigned U.S. patent application Ser. No. 09/312,997 filed on May 17, 1999, which is hereby incorporated herein by reference.

The diaper 20 may also include side panels 30 disposed in the back waist region 38, in the front waist region 36, or in both the front waist region 36 and the back waist region 38 as shown, for example, in FIG. 1 and other figures. The side panels 30 may be constructed in any suitable configuration known in the art. The side panels 30 may be elastically extensible. An exemplar of an elastic side panel is described in U.S. Pat. No. 5,669,897 issued Sep. 23, 1997, which is hereby incorporated herein by reference.

The diaper 20 may include at least one leg cuff 32 as shown, for example, in FIG. 1 and other figures. Leg cuffs 32 are known variously in the art as leg cuffs, leg bands, side flaps, barrier cuffs, and/or elastic cuffs. The leg cuff 32 may be substantially inelastic or may be elastically extensible to dynamically fit at the wearer's leg. The leg cuff 32 may be constructed in any suitable configuration known in the art, including those described in U.S. Pat. No. 4,695,278 issued Sep. 22, 1987, and U.S. Pat. No. 4,795,454 issued Jan. 3, 1989, which are hereby incorporated herein by reference.

Figure 13:
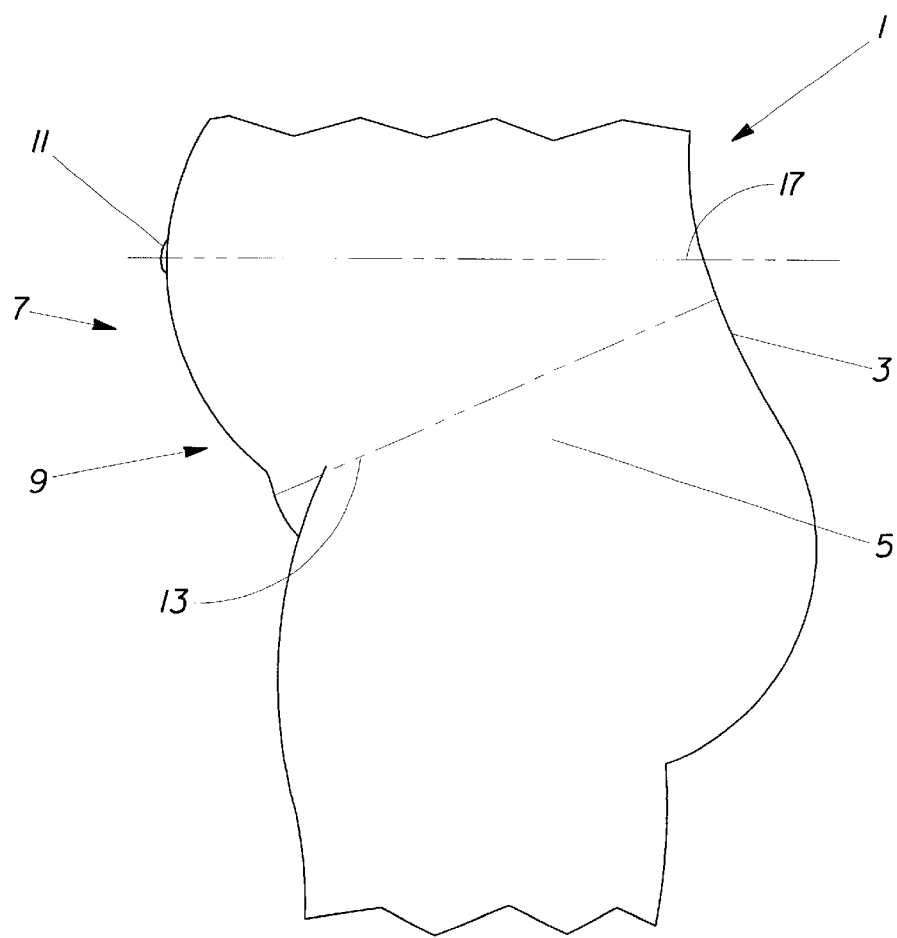
FIG. 13 is a side view of a portion of the torso of a wearer, such as an ambulatory child, in an upright or standing position.
Figure 14:
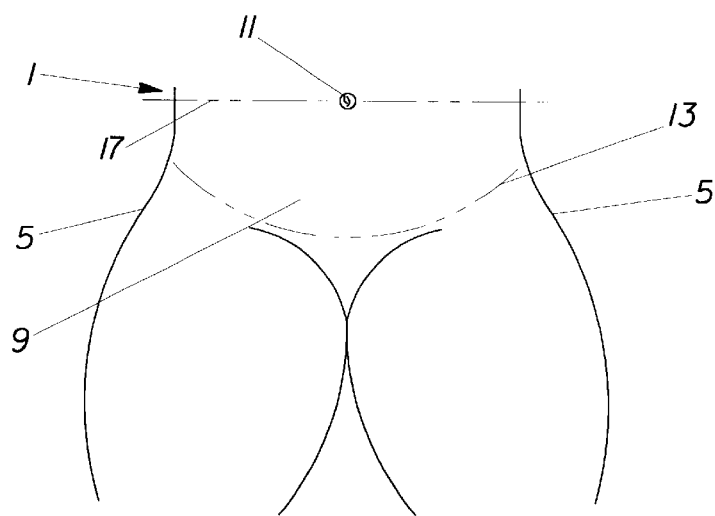
FIG. 14 is a front view of a portion of the torso of a wearer, such as an ambulatory child, in an upright or standing position.

The diaper 20 of the present invention also includes at least one diagonal support member 200. Examples of the diagonal support member 200 are shown in FIG. 1, FIG. 2, and other figures. The diagonal support member 200 is designed to support the diaper 20 on the body substantially in the diagonal support zone 13. In FIG. 13, which shows a partial side view of the torso 1 of an infant, the anatomical location of the diagonal support zone 13 is shown to lie generally across the small of the back 3, over the hips 5, and across the lower abdomen 9 of the wearer's body. The diagonal support zone 13 is angled downward in the front of the body relative to the waistline plane 17. In the partial front view of the torso 1 of an infant of FIG. 14, the diagonal support zone 13 is shown to lie generally across the lower abdomen 9 of the wearer's body.

Figure 15:
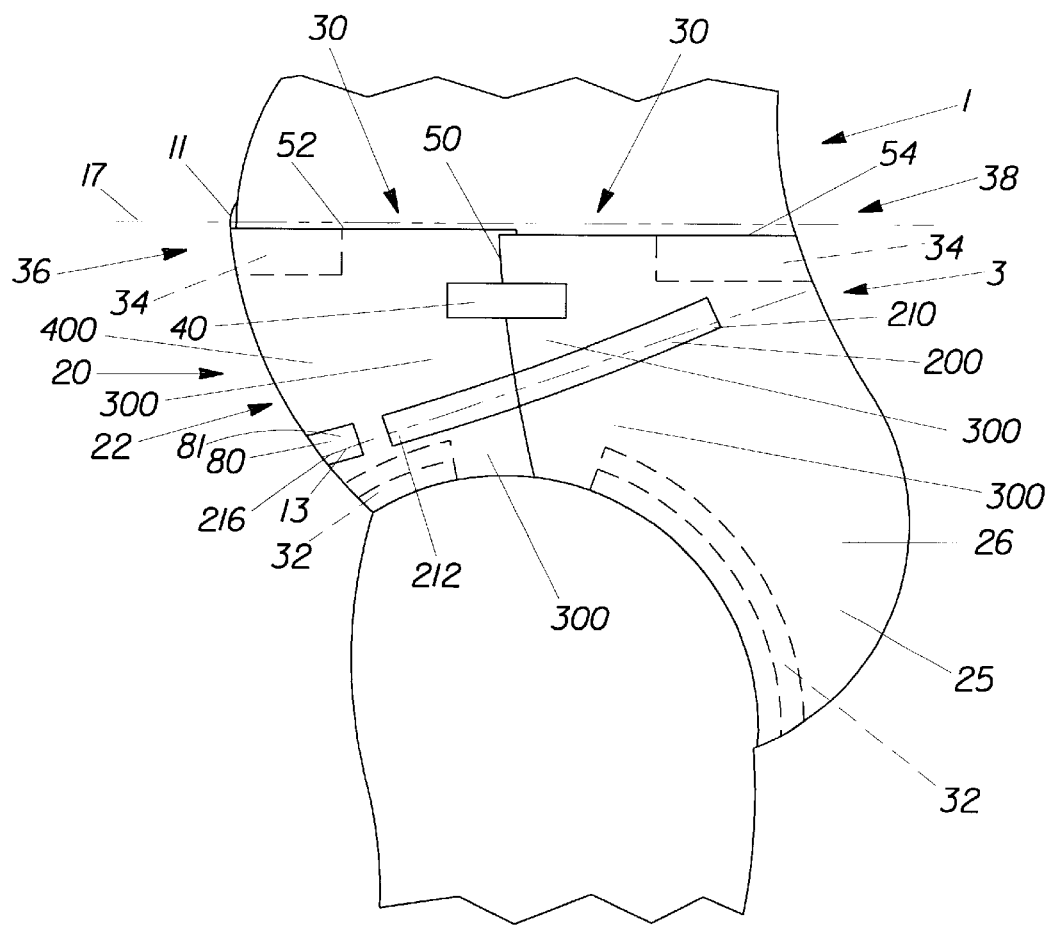
FIG. 15 is a side view of a portion of the torso of a wearer, such as an ambulatory child, in an upright or standing position, wearing an absorbent article of the present invention.
Figure 16:
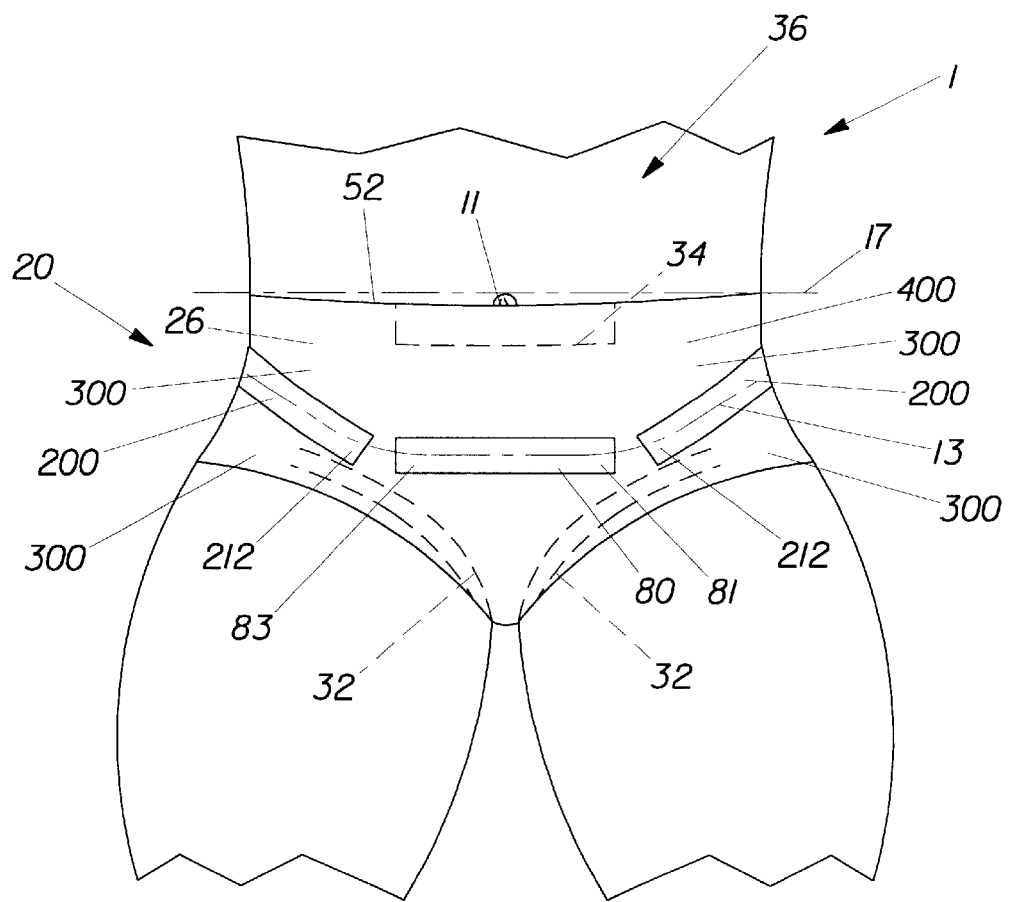
FIG. 16 is a front view of a portion of the torso of a wearer, such as an ambulatory child, in an upright or standing position, wearing an absorbent article of the present invention.

The diagonal support member 200 preferably is disposed in the diaper 20 so as to lie at least partially in the diagonal support zone 13 of the wearer's body when the diaper 20 is worn. FIG. 15 shows a partial side view of the torso 1 of an infant and the diaper 20 as worn. As can be seen by reference between FIG. 13 and FIG. 15, the front end edge 52 and the back end edge 54 lie substantially parallel to the waistline plane 17 and the diagonal support member 200 lies substantially parallel to the diagonal support zone 13 when the diaper 20 is worn. FIG. 16 shows a partial front view of the torso 1 of an infant and the diaper 20 as worn. It can also be seen by reference between FIG. 14 and FIG. 16 that the diagonal support member 200 lies substantially parallel to the diagonal support zone 13 when the diaper 20 is worn.

The diagonal support member 200 has a first end 210 and a second end 212. The first end 210 preferably is disposed so as to lie substantially adjacent the back waist region 38 of the diaper 20 when the diaper 20 is worn. The second end 212 preferably is disposed so as to lie substantially adjacent the wearer's lower abdomen 9 when the diaper 20 is worn. The first end 210 and the second end 212 define a major diagonal axis 216 of the diagonal support member 200. The major diagonal axis 216 preferably is substantially parallel to the diagonal support zone 13 of the wearer's body when the diaper 20 is worn. In various embodiments, the major diagonal axis 216 may preferably be disposed at an angle greater than about 5 degrees or at an angle greater than about 15 degrees relative to the lateral centerline 110 of the diaper 20. Likewise, in various embodiments, the major diagonal axis 216 may preferably be disposed at an angle of about 60 degrees or less or at an angle of 45 degrees or less relative to the lateral centerline 110. An angle of about 30 degrees between the major diagonal axis 216 and the lateral centerline 110 has been found to be suitable over a wide range of sizes of wearers and of the diaper 20.

The diagonal support member 200 may be disposed at least partially interiorly to the formed diaper 20 adjacent the inner surface 23 of the containment assembly 22. Alternatively, the diagonal support member 200 may be disposed at least partially exteriorly to the formed diaper 20 adjacent the outer surface 25 of the containment assembly 22. Furthermore, the diagonal support member 200 may be disposed at least partially between the topsheet 24 and the backsheet 26. For example, in the embodiment shown in FIG. 2, the diagonal support member 200 is disposed exteriorly to the formed diaper 20, while in the embodiment shown in FIG. 7, the diagonal support member 200 is disposed between the topsheet 24 and the backsheet 26 of diaper 20.

In general, the diagonal support member 200 may be of any suitable size and/or shape. The diagonal support member 200 has a width 218 which is measured substantially at a right angle to the major diagonal axis 216. The diagonal support member 200 may have any width 218 suitable for the avoidance of pressure marking on the wearer's body and for fitting into the bodily contours generally defining the diagonal support zone 13. In some embodiments, the diagonal support member 200 preferably has a width 218 in the range of about 10 millimeters to about 50 millimeters. It has been found that a width 218 of the diagonal support member 200 of about 25 millimeters is suitable over a wide range of sizes of wearers and of the diaper 20.

The diagonal support member 200 may comprise any material known in the art which is suitable for the purpose of supporting the diaper 20 as described above. The diagonal support member 200 preferably is compliant, soft-feeling, and non-irritating to the skin such that it has minimal negative effect on the wearer's comfort and/or the visual and/or tactile perception of the user. The diagonal support member 200 preferably is elastically extensible at least in a direction substantially parallel to its major diagonal axis 216, but may be substantially inelastic in nature. Suitable materials for use in the construction of the diagonal support member 200 include materials used in other elements of the diaper 20, such as topsheet 24 material, backsheet 26 material, waist feature 34 material, side panel 30 material, leg cuff 32 material, elastic strip material, and the like. The diagonal support member 200 may comprise a single layer or a laminate of suitable materials. Such a laminate may include, for example, nonwoven material, film, formed film, scrim material, foam, and/or strip material. In some embodiments, the diagonal support member 200 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, which is hereby incorporated herein by reference. Also, the diagonal support member 200 may comprise incrementally stretched material formed by methods such as ring rolling between meshed corrugated rolls, stamping with meshing platens, and the like. Examples of incremental stretching methods and suitable incrementally stretched materials are described in U.S. Pat. No. 5,167,897 issued Dec. 1, 1992, which is hereby incorporated herein by reference.

The diagonal support member 200 may be joined to the backsheet 26, the topsheet 24, to both the backsheet 26 and the topsheet 24, and/or to any other element of the diaper 20 by any attachment means known in the art which is suitable for the materials involved. For example, the attachment means may include any of those listed above in reference to the backsheet 26.

Figure 5:
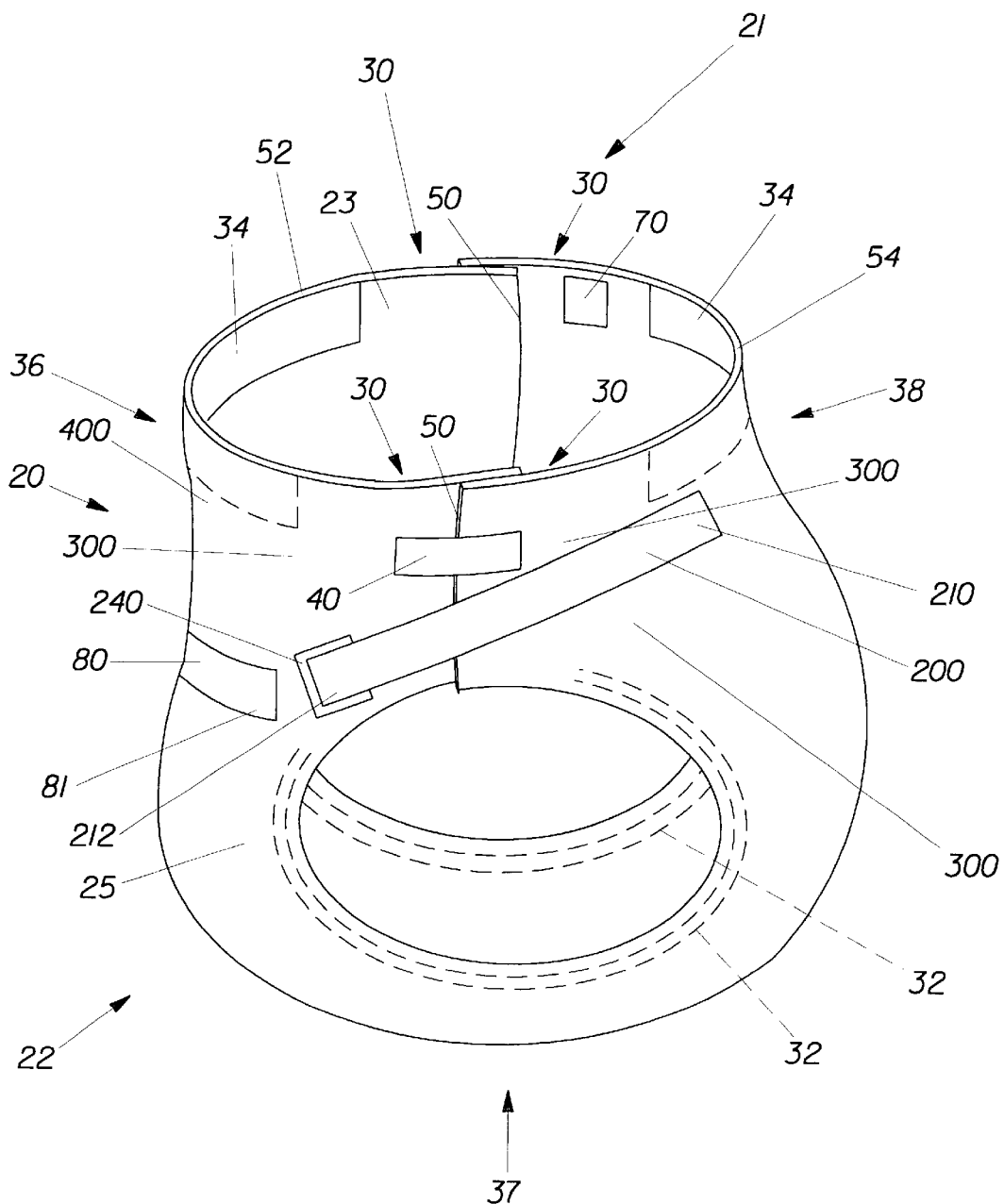
FIG. 5 is a side perspective view of an alternative embodiment of the absorbent article of the present invention in assembled form.
Figure 6:
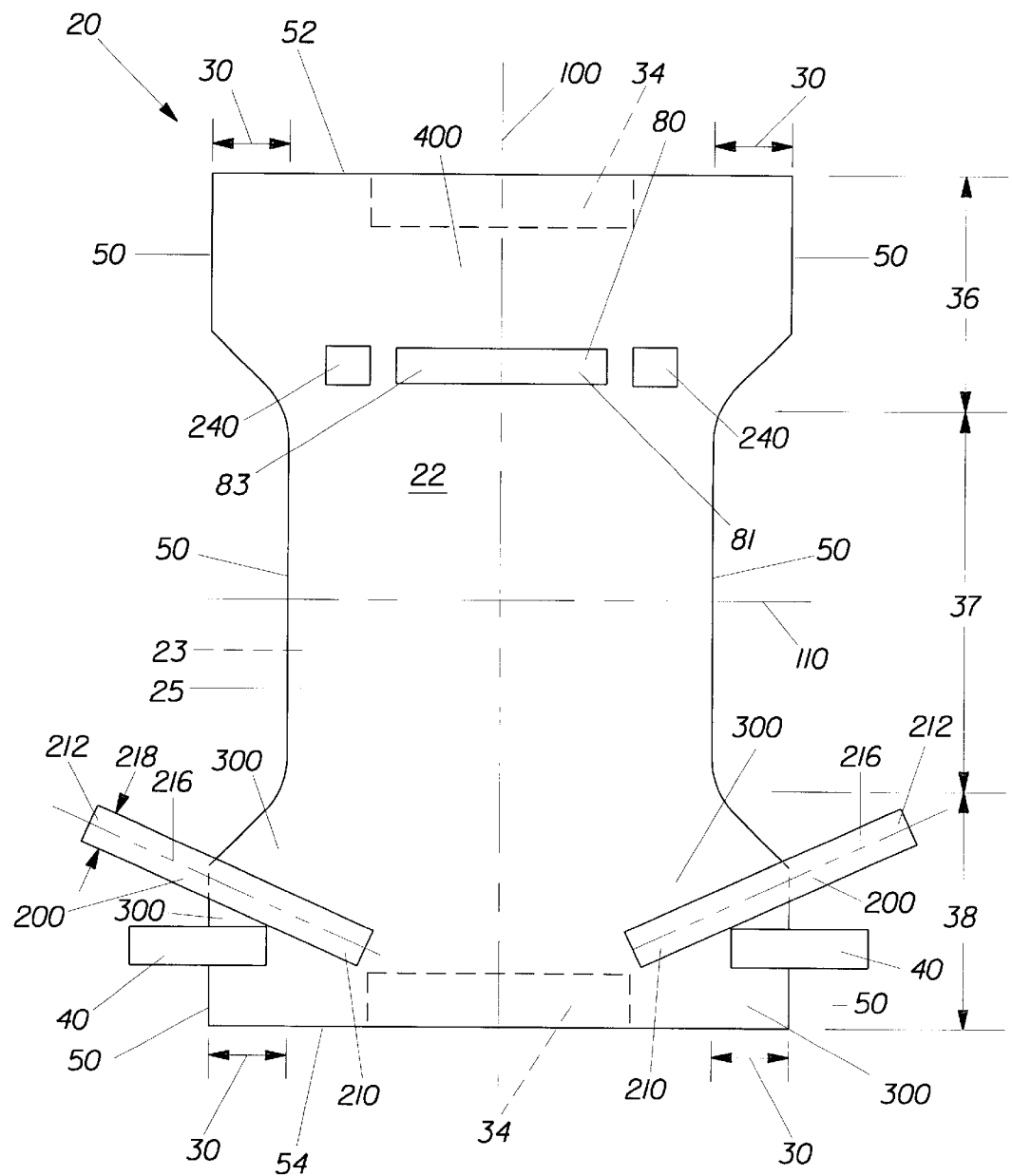
FIG. 6 is a simplified plan view of the absorbent article in FIG. 5, laid out flat and showing various sections and structural elements.

The diagonal support member 200 may be joined to another element of the diaper 20 at least at or near the first end 210 and the second end 212 and/or may be joined along any portion of its length or substantially its entire length. Alternatively, at least some portion of the diagonal support member 200 may be joined to another element of the diaper 20 and at least the first end 210 and/or the second end 212 may be unjoined to any other element of the diaper 20. In some embodiments, the unjoined first end 210 or second end 212 of the diagonal support member 200 may have at least one diagonal support fastening system 240. For example, the embodiment of diaper 20 shown in FIG. 2 has the second end 212 of the diagonal support member 200 joined to the containment assembly 22 substantially adjacent the lower abdomen 9 of the wearer's body when the diaper 20 is worn and the first end 210 of the diagonal support member 200 fastened substantially adjacent the back waist region 38 of the diaper 20 by means of the diagonal support fastening system 240. In the alternative embodiment shown in FIG. 5 and in FIG. 6, the diaper 20 has the first end 210 of the diagonal support member 200 joined to the containment assembly 22 substantially adjacent the back waist region 38 of the diaper 20 and the second end 212 fastened substantially adjacent the lower abdomen 9 of the wearer's body, when the diaper 20 is worn, by means of the diagonal support fastening system 240. The diagonal support fastening system 240 may comprise any of the fastening means listed above in reference to the fastening system 40 and/or any other suitable fastening means. The diagonal support fastening system 240 may be openable and refastenable to facilitate adjustment of the fit of the diaper 20 on the body of the wearer. Furthermore, the diagonal support fastening system 240 may include distinctive marks denoting various potential fastening positions of the unjoined first end 210 or second end 212 of the diagonal support member 200.

Figure 10:
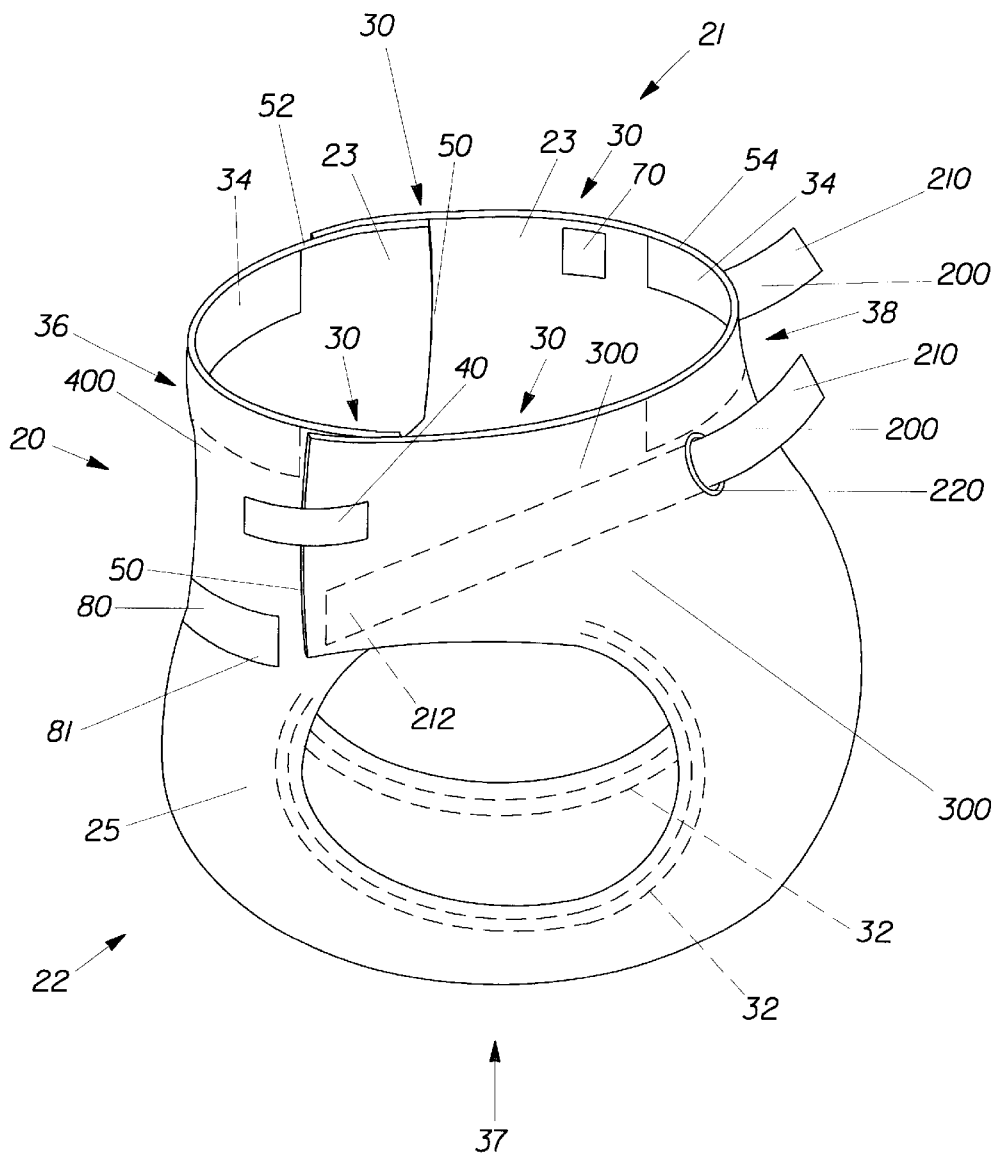
FIG. 10 is a side perspective view of an alternative embodiment of the absorbent article of the present invention in assembled form.

In some embodiments, the unjoined first end 210 or second end 212 of the diagonal support member 200 may pass through a grommet, eyelet or ring structure 220 enabling the diagonal support member 200 to be used as a drawstring or cinch strap. For example, in the embodiment shown in FIG. 10, the diagonal support member 200 is partially disposed between the topsheet 24 and the backsheet 26, the first end 210 of the diagonal support member 200 is unjoined, and this unjoined first end 210 emerges through a grommet 220 for use of the diagonal support member 200 as a drawstring.

Figure 7:
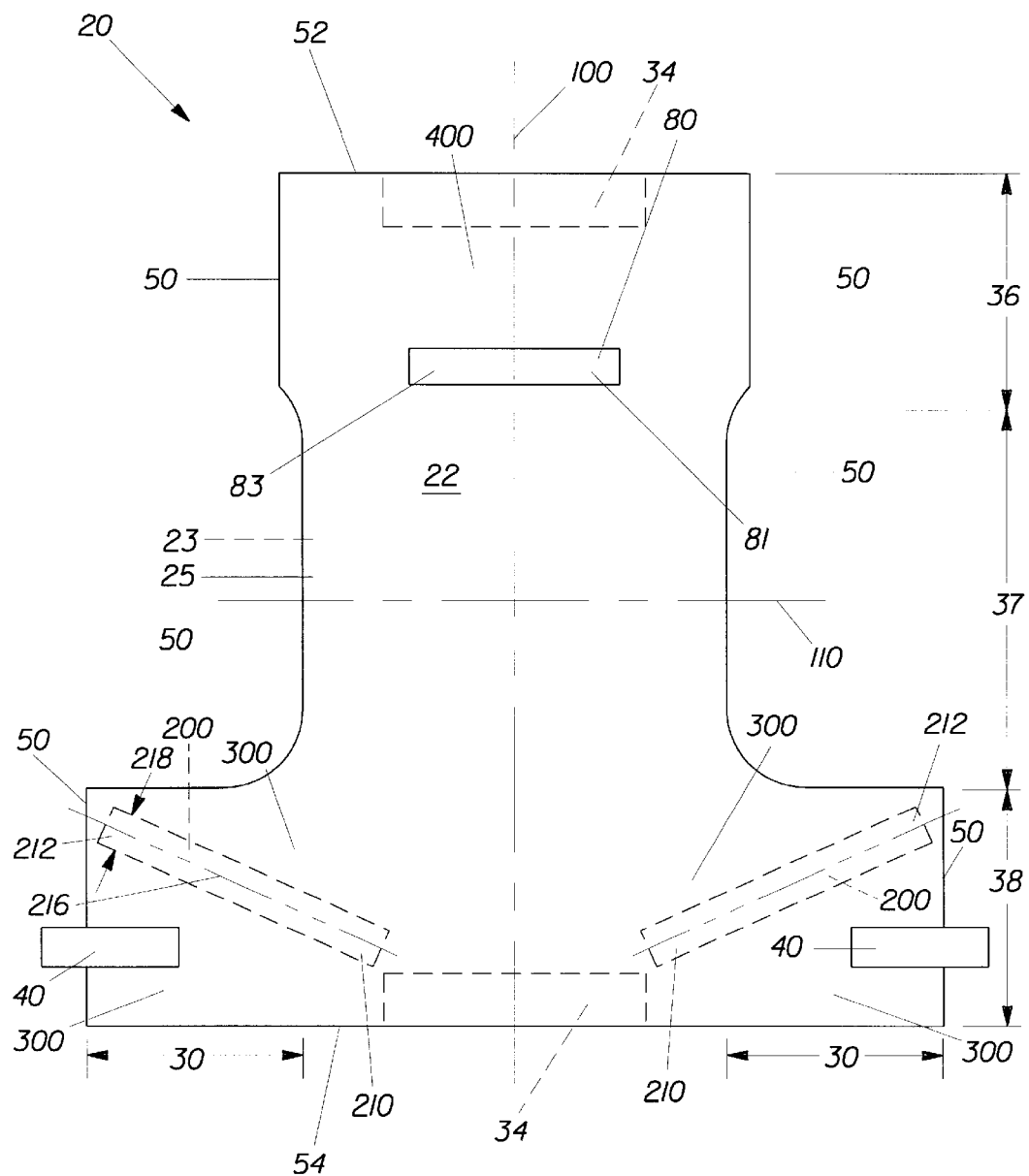
FIG. 7 is a simplified plan view of an alternative embodiment of the absorbent article of the present invention, laid out flat and showing various sections and structural elements.

In some embodiments, the diagonal support member 200 may comprise a unitary structure spanning between the first end 210 and the second end 212. For example, in the embodiment shown in FIG. 2, the diagonal support member 200 is disposed exteriorly to the formed diaper 20 and spans between the first end 210 and the second end 212. Another example of a diagonal support member 200 comprising a unitary structure is shown in the embodiment of FIG. 7, in which the diagonal support member 200 is disposed substantially between the topsheet 24 and the backsheet 26 of diaper 20. In this embodiment, the back end edge 54 has a greater length than the front end edge 52. Thus, the side edges 50 in the front waist region 36 and the back waist region 38 lie circumferentially less distantly from the longitudinal centerline 100 in the front waist region 36 than in the back waist region 38 when the diaper 20 is worn. Anatomically, in this embodiment, the side edges 50 in the front waist region 36 and the back waist region 38 of the diaper 20 lie substantially adjacent the lower abdomen 9 when the diaper 20 is worn. Thus, in this embodiment, the diagonal support member 200 may comprise a unitary structure spanning between the first end 210 and the second end 212.

Figure 9:
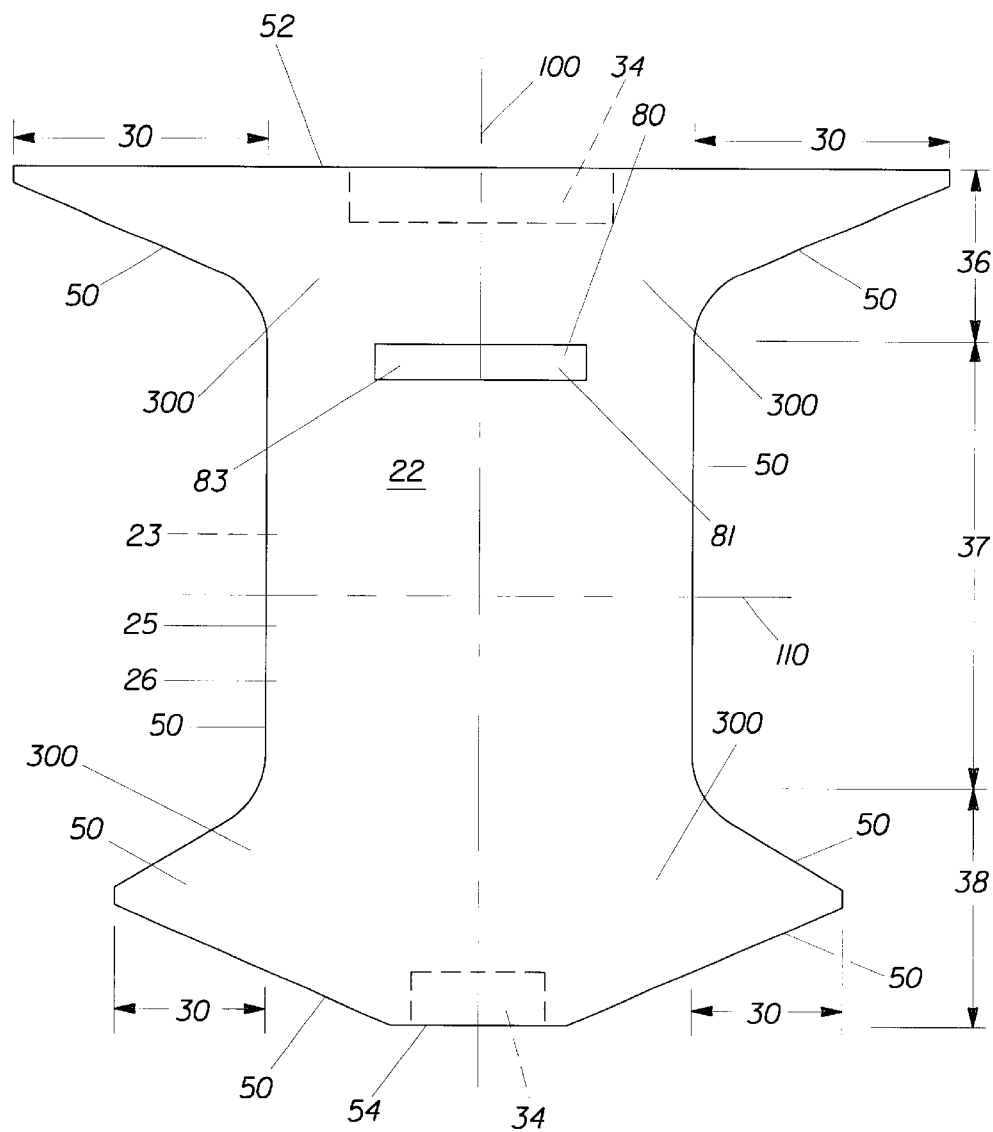
FIG. 9 is a simplified plan view of the absorbent article in FIG. 8 prior to closure, laid out flat and showing various sections and structural elements.

Another exemplary embodiment of the diaper 20 in which the diagonal support member 200 may comprise a unitary structure is shown in FIG. 8 and FIG. 9. In this embodiment, the side edges 50 of the diaper 20 in the front waist region 52 and the back waist region 54 are substantially non-parallel to the longitudinal centerline 100. Instead, the side edges 50 in the front waist region 52 and the back waist region 54 are substantially angled relative to the longitudinal centerline 100 so as to lie substantially in the diagonal support zone 13 of the wearer's body when the diaper 20 is worn. As shown in FIG. 8, the opposing side edges 50 in the front waist region 52 and the back waist region 54 may be joined by seams or welds 42, as described above in reference to the pre-closed form of the diaper 20. In such an embodiment, the material which is bonded in the seams or welds 42 may have suitable characteristics, as described above, to substantially constitute the diagonal support member 200. Alternatively, the diagonal support member 200 may comprise at least one additional element disposed substantially parallel to and in close proximity to side edges 50 in the front waist region 52 and the back waist region 54 which are angled as shown in FIG. 9.

Figure 12:
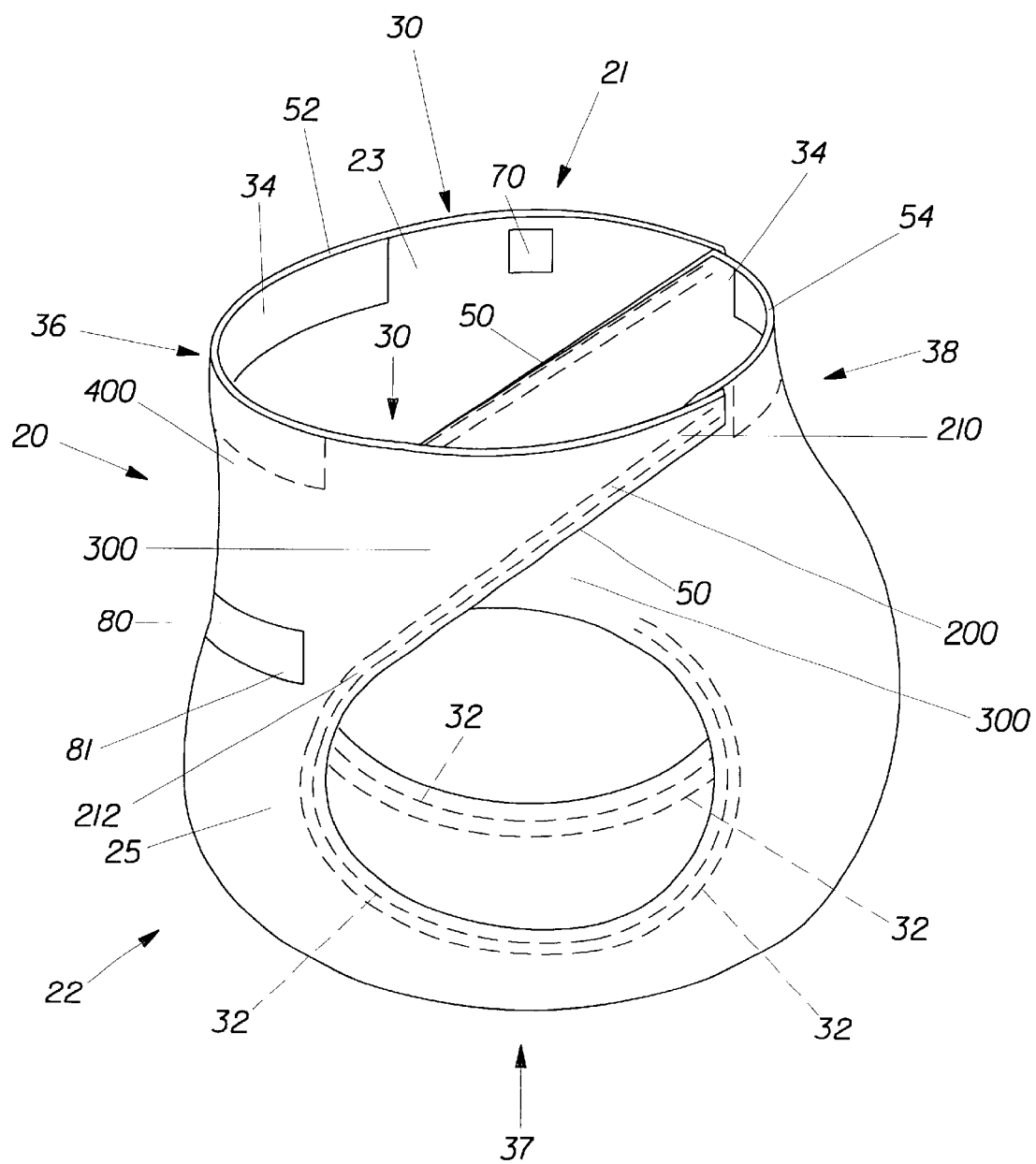
FIG. 12 is a side perspective view of an alternative embodiment of the absorbent article of the present invention in assembled form.

In some embodiments, the diagonal support member 200 and the leg cuff 32 may constitute a substantially unitary structure, as shown in the exemplary embodiment of FIG. 12. For example, an elastically extensible diagonal support member 200 may comprise an extension of the material forming an elastically extensible leg cuff 32. In another example, an elastically extensible leg cuff 32 may comprise an extension of the material forming an elastically extensible diagonal support member 200. In such embodiments, the substantially unitary structure forming the diagonal support member 200 and the leg cuff 32 may have specific properties in specific portions. For example, an elastically extensible unitary structure may have a first elastic modulus in the portion forming the leg cuff 32 and a second elastic modulus in the portion forming the diagonal support member 200. Similarly, the thickness, width, material composition, and/or some other property may be specific to specific portions of what is nonetheless a substantially unitary structure forming the diagonal support member 200 and the leg cuff 32.

Figure 11:
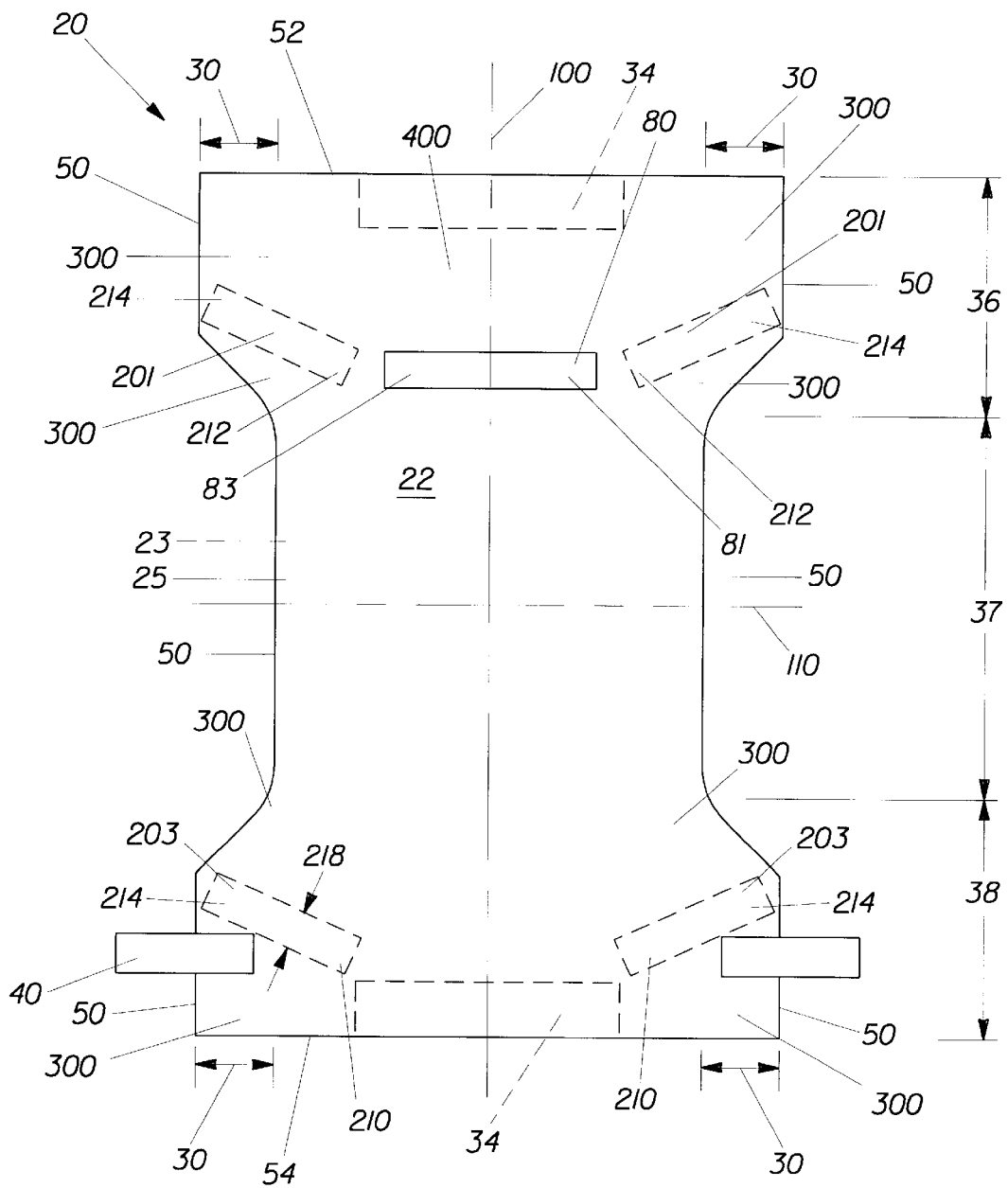
FIG. 11 is a simplified plan view of an alternative embodiment of the absorbent article of the present invention, laid out flat and showing various sections and structural elements.

In some embodiments, the back end edge 54 and the front end edge 52 may have substantially equal lengths and thus the side edges 50 in the front waist region 36 and the back waist region 38 may lie substantially circumferentially equidistantly from the longitudinal centerline 100 in the front waist region 36 and in the back waist region 38 when the diaper 20 is worn. Anatomically, in such an embodiment, the side edges 50 in the front waist region 36 and the back waist region 38 lie substantially circumferentially equidistantly from the navel 11 and the small of the back 3 when the diaper 20 is worn. In such embodiments, the diagonal support member 200 may comprise two or more discrete elements. For example, in the embodiments shown in FIG. 1 and FIG. 11, the back end edge 54 and the front end edge 52 have substantially equal lengths and the diagonal support member 200 is disposed substantially between the topsheet 24 and the backsheet 26. As shown in FIG. 1 and FIG. 11, the diagonal support member 200 may comprise at least one front diagonal support element 201 disposed substantially in the front waist region 36 and at least one back diagonal support element 203 disposed substantially in the back waist region 38 of the diaper 20. The front diagonal support element 201 and the back diagonal support element 203 preferably are aligned substantially along the major diagonal axis 216 of the diagonal support member 200 such that they function cooperatively to support the diaper 20 on the body substantially in the diagonal support zone 13 when the diaper 20 is worn, that is, such that when the diaper 20 is worn, they act cooperatively substantially like a diagonal support member 200 comprising a unitary structure.

In embodiments in which the diagonal support member 200 comprises two or more discrete elements, the intermediate ends 214 may be fastened to each other and/or may be joined and/or fastened to other elements of the diaper 20, as described above. Alternatively, at least one of the intermediate ends 214 may be unjoined to any other element of the diaper 20. As described above in reference to the first end 210 and the second end 212, such an unjoined intermediate end 214 of the diagonal support member 200 may have at least one diagonal support fastening system 240 and/or may pass through a grommet, eyelet, or ring structure 220 enabling the diagonal support member 200 to be used as a drawstring or cinch strap.

The diagonal support member 200 preferably bears the major portion of the weight of the diaper 20, especially when the diaper 20 is loaded with excreta. In addition, the diagonal support member 200 preferably resists downward force caused by changes in bodily shape or dimension such as an expansion of the abdomen and/or a transition from a sitting posture to a standing posture. In order to support the diaper 20 on the body substantially in the diagonal support zone 13 of the wearer's body, the diagonal support member 200 preferably contributes to a diagonal hoop force generally parallel to the diagonal support zone 13. This diagonal hoop force preferably limits the diagonal circumferential expansion of the diaper 20 and thereby prevents the diaper 20 from sliding downward to a position substantially below the diagonal support zone 13. The diagonal hoop force may be of any magnitude suitable for the size of the diaper 20 and/or the size of the wearer's body and/or the materials involved. In various embodiments, the magnitude of the diagonal hoop force may preferably be greater than about 30 grams force, greater than about 65 grams force, or greater than about 180 grams force when the diaper 20 is worn. Likewise, in various embodiments, the magnitude of the diagonal hoop force may preferably be less than about 2000 grams force, less than about 570 grams force, or less than about 300 grams force when the diaper 20 is worn. It has been found that a diagonal hoop force of a magnitude of about 250 grams force when the diaper 20 is worn is suitable over a wide range of sizes of wearers and sizes of the diaper 20. The magnitude of the diagonal hoop force preferably is minimally affected by bodily movement of the wearer and preferably varies minimally over the range of bodily postures assumed by the wearer while the diaper 20 is worn. Thus, in embodiments in which the diagonal support member 200 is elastically extensible, the magnitude of the force exerted by the diagonal support member 200 preferably varies only minimally over the range of bodily postures assumed by the wearer while the diaper 20 is worn.

The diaper 20 of the present invention may also include at least one lateral reinforcement member 80 as shown in FIG. 1 and other figures. The lateral reinforcement member 80 preferably laterally reinforces and/or supports the containment assembly 22 in the area across the lower abdomen 9 of the body. The lateral reinforcement member 80 preferably transfers laterally at least a portion of the force exerted by the diagonal support member 200 when the diaper 20 is worn. The lateral reinforcement member 80 has a first reinforcement member end 81 and a second reinforcement member end 83. The lateral reinforcement member 80 preferably is disposed between the front end edge 52 and the lateral centerline 110 such that at least either the first reinforcement member end 81 or the second reinforcement member end 83 preferably lies substantially adjacent the second end 212 of the diagonal support member 200 when the diaper 20 is worn. At least one of the waist edges 62 of the absorbent core 28 may be disposed between the lateral reinforcement member 80 and the front end edge 52 of the diaper 20.

The lateral reinforcement member 80 may comprise any material suitable for the purpose of reinforcing and supporting the containment assembly 22 as described above. Suitable materials include those listed above in reference to the diagonal support member 200. The lateral reinforcement member 80 preferably is at least laterally elastically extensible, but may be substantially inelastic in nature.

The lateral reinforcement member 80 may be joined to the backsheet 26, the topsheet 24, to both the backsheet 26 and the topsheet 24, and/or to any other element of the diaper 20 by any attachment means known in the art which is suitable for the materials involved. For example, the attachment means may include any of those listed above in reference to the backsheet 26. The lateral reinforcement member 80 may be joined to another element of the diaper 20 at least at or near the first reinforcement member end 81 and the second reinforcement member end 83 and/or may be joined along any portion of its length or substantially its entire length.

The lateral reinforcement member 80 may be disposed at least partially interiorly to the formed diaper 20 adjacent the inner surface 23 of the containment assembly 22. Alternatively, the lateral reinforcement member 80 may be disposed at least partially exteriorly to the formed diaper 20 adjacent the outer surface 25 of the containment assembly 22. Furthermore, the lateral reinforcement member 80 may be disposed at least partially between the topsheet 24 and the backsheet 26.

The diaper 20 of the present invention may also include a supportive loop segment formed by at least a portion of the diagonal support member 200 and at least a portion of the lateral reinforcement member 80. The supportive loop segment preferably lies at least partially in the diagonal support zone 13 of the wearer's body when the diaper 20 is worn. The supportive loop segment may be joined to the backsheet 26 and/or to the topsheet 24 and/or to any other element of the diaper 20 by any attachment means known in the art which is suitable for the materials involved, including those listed above in reference to the backsheet 26. In some embodiments, the supportive loop segment may by unjoined, that is, not joined to any other element of the diaper 20. For example, in an embodiment of the diaper 20 in which the unjoined supportive loop segment comprises lateral reinforcement member 80 disposed between the topsheet 24 and the backsheet 26 and diagonal support member 200 disposed between the topsheet 24 and the backsheet 26, the diagonal support member 200 may have a first end 210 which is unjoined, and this unjoined first end 210 may emerge through a grommet, eyelet, or ring structure 220 for use of the supportive loop segment 280 as a drawstring or cinch strap.

The diaper 20 of the present invention may also include at least one side covering panel 300 as shown, for example, in FIG. 1 and other figures. The side covering panel 300 preferably is disposed adjacent at least a portion of the diagonal support member 200 and covers at least a portion of the wearer's body which the diagonal support member 200 is substantially adjacent when the diaper 20 is worn. The side covering panel 300 preferably transfers minimal force from adjacent elements of the diaper 20 to the diagonal support member 200 such that the functionality of the diagonal support member 200 is minimally affected by force exerted by the adjacent elements. Such force may, for example, result from changes in bodily shape or dimension such as an expansion of the abdomen and/or a transition from a sitting posture to a standing posture.

The side covering panel 300 may comprise any material known in the art which is suitable for the purpose of transferring minimal force from adjacent elements of the diaper 20 to the diagonal support member 200, as described above. The side covering panel 300 preferably is compliant, soft-feeling, and non-irritating to the skin such that it has minimal negative effect on the wearer's comfort and/or the visual and/or tactile perception of the user. The side covering panel 300 may be elastically extensible in at least one direction or may be substantially inelastic in nature. For example, a substantially inelastic side covering panel 300 may comprise an extra amount of material or folded, crepe, and/or pleated material providing sufficient expandability such that the diagonal support member 200 is minimally affected by force exerted by other elements of the diaper 20 throughout the range of bodily movement. An elastically extensible side covering panel 300 may, for example, comprise a low modulus elastic material providing minimal contractive force to conform the material of the side covering panel 300 to the bodily contour, while providing insufficient force to substantially constrain the diagonal support member 200, and while providing sufficient expandability to transfer minimal force to the diagonal support member 200 throughout the range of bodily movement. The term "low modulus" herein refers to a material and/or an element of the diaper 20 having a low elastic modulus relative to that of other materials used in the diaper 20. Such a low modulus element is easily elongated upon the application of tension and will exert minimal contractive force while in the elongated state. For example, such a low modulus elastic material may have an elastic modulus in the range of about 25 grams force to about 75 grams force per unit strain on a 25 millimeter wide piece, although a material having an elastic modulus in another range may also be suitable. The term "unit strain" herein refers to the elongation under tension of an element having a starting length to a length twice the starting length, i.e., an elongation of one unit of length for each unit of starting length. In some embodiments, the side covering panel 300 may comprise a structural elastic-like film ("SELF") web and/or an incrementally stretched material as described above in reference to the diagonal support member 200.

Suitable materials for use in the construction of the side covering panel 300 include materials used in other elements of the diaper 20, such as topsheet 24 material, backsheet 26 material, waist feature 34 material, side panel 30 material, leg cuff 32 material, elastic strip material, and the like. The side covering panel 300 may comprise a single layer or a laminate of suitable materials. Such a laminate may include, for example, nonwoven material, film, formed film, scrim material, foam, and/or strip material.

The diaper 20 of the present invention may include at least one front covering panel 400 as shown, for example, in FIG. 1 and other figures. The front covering panel 400 preferably is disposed in the front waist region 36 and covers at least a portion of the wearer's body which the front waist region 36 is substantially adjacent when the diaper 20 is worn. The front covering panel 400 preferably transfers minimal downward force from adjacent elements of the diaper 20 to the waist feature 34 and/or the front end edge 52. An example of such downward force is the weight of the diaper 20. By transferring minimal downward force from adjacent elements of the diaper 20, the front covering panel 400 preferably minimizes the portion of the weight of the diaper 20 that is borne by the waist feature 34 versus the portion of the weight that is borne by the diagonal support member 200. In some embodiments of the diaper 20, the front covering panel 400 preferably is disposed between the lateral reinforcement member 80 and the front end edge 52. In such an embodiment, the front covering panel 400 preferably transfers a minimal portion of the weight borne by the lateral reinforcement member 80 to the waist feature 34 and/or the front end edge 52 such that weight borne by the lateral reinforcement member 80 generally is transferred to the diagonal support member 200, rather than to the front end edge 52 and/or the waist feature 34. Downward force on the front end edge 52 and/or the waist feature 34 may also be caused by movement and/or changes in posture of the wearer. For example, raising the arms and/or straightening the spine of the wearer may result in longitudinal tension being generated in the front waist region 36 and downward force being exerted. The front covering panel 400 preferably transfers a minimal portion of such downward force caused by movement and/or changes in posture of the wearer to the waist feature 34 and/or the front end edge 52. The front covering panel 400 may comprise any material known in the art which is suitable for the purpose of transferring minimal downward force to the waist feature 34 and/or the front end edge 52, including those materials described above in reference to the side covering panel 300.

The disclosures of all patents, patent applications, and any corresponding patents which issue thereon, as well as any corresponding published foreign patent applications, and publications mentioned throughout this description are hereby incorporated herein by reference. It is expressly not admitted, however, that any of the documents incorporated herein by reference teach or disclose the present invention.

While various embodiments and/or individual features of the present invention have been illustrated and described, it would be obvious to those skilled in the art that various other changes and modifications can be made without departing from the spirit and scope of the invention. As will also be apparent to the skilled practitioner, all combinations of the embodiments and features taught in the foregoing disclosure are possible and can result in preferred executions of the invention. It is therefore intended to cover in the appended claims all such changes and modifications as are within the scope of this invention.

What is claimed is:

1. A disposable absorbent article for fitting about a wearer's body to contain excreta and/or bodily exudates, the wearer's body having a lower abdomen, hip joints, a small of the back, and a diagonal support zone lying across the small of the back over the hip joints and across the lower abdomen, the absorbent article comprising:
   a) a containment assembly having a longitudinal centerline, a lateral centerline, a front waist region, a back waist region opposed to the front waist region, a crotch region disposed between the front waist region and the back waist region, a front end edge, a back end edge, side edges, a topsheet, a backsheet, and an absorbent core disposed at least partially between the topsheet and the backsheet;
   b) at least one side panel in the back waist region extending laterally outwardly from the longitudinal centerline farther than the crotch region extends laterally at the lateral centerline and having a laterally extending edge forming a portion of the back end edge;
   c) at least one waist feature disposed substantially adjacent either the front end edge or the back end edge; and
   d) at least one diagonal support member having a first end and a second end defining a major diagonal axis oriented nonparallel to the lateral centerline and nonparallel to the laterally extending edge of the at least one side panel when the absorbent article is in a flat uncontracted condition, the diagonal support member disposed such that when the absorbent article is worn the diagonal support member lies at least partially in the diagonal support zone of the wearer's body and closer to the lateral centerline than the nearer of the front end edge and the back end edge, the first end lying substantially adjacent the back waist region and the second end lying substantially adjacent the lower abdomen and closer to the lateral centerline than the first end.

2. The disposable absorbent article of claim 1 wherein the containment assembly further includes at least one side covering panel disposed adjacent at least a portion of the diagonal support member, the side covering panel covering at least a portion of the wearer's body which the diagonal support member is substantially adjacent when the absorbent article is worn.

3. The disposable absorbent article of claim 1 wherein the containment assembly further includes at least one front covering panel disposed in the front waist region, the front covering panel covering at least a portion of the wearer's body which the front waist region is substantially adjacent when the absorbent article is worn.

4. The disposable absorbent article of claim 1 wherein at least a portion of the diagonal support member is elastically extensible at least in a direction substantially parallel to the major diagonal axis of the diagonal support member.

5. The disposable absorbent article of claim 1 wherein the containment assembly has an inner surface having a coefficient of static friction to the wearer's body, the absorbent article further including at least one high friction retention zone disposed at least partially on the inner surface of the containment assembly in either the front waist region or the back waist region, the high friction retention zone having a coefficient of static friction to the wearer's body at least about twice the coefficient of static friction to the wearer's body of the inner surface of the containment assembly.

6. The disposable absorbent article of claim 1 wherein at least a portion of the waist feature is elastically extensible at least laterally.

7. The disposable absorbent article of claim 1 further including at least one fastening system, the fastening system disposed at least partially adjacent at least a portion of the side edges of the front waist region and/or the back waist region such that the fastening system substantially maintains the front waist region and the back waist region in a hoop configuration.

8. The disposable absorbent article of claim 1 further including at least one leg cuff, the diagonal support member and the leg cuff forming a substantially unitary structure.

9. The disposable absorbent article of claim 1 wherein at least either the first end or the second end of the diagonal support member is unjoined to any other element of the absorbent article.

10. The disposable absorbent article of claim 9 wherein the unjoined first end or second end of the diagonal support member has at least one diagonal support fastening system.

11. The disposable absorbent article of claim 1 wherein the diagonal support member comprises two or more discrete elements, the discrete elements aligned substantially along the major diagonal axis of the diagonal support member such that the discrete elements function cooperatively to support the absorbent article substantially in the diagonal support zone of the wearer's body when the absorbent article is worn.

12. The disposable absorbent article of claim 11 wherein the discrete elements of the diagonal support member have intermediate ends, at least one of the intermediate ends of at least one of the discrete elements having at least one diagonal support fastening system.

13. The disposable absorbent article of claim 1 wherein the containment assembly further includes at least one lateral reinforcement member having a first reinforcement member end and a second reinforcement member end, the lateral reinforcement member disposed between the front end edge and the lateral centerline of the containment assembly such that at least either the first reinforcement member end or the second reinforcement member end lies substantially adjacent the second end of the diagonal support member when the absorbent article is worn.

14. The disposable absorbent article of claim 13 wherein at least a portion of the lateral reinforcement member is elastically extensible at least laterally.

15. The disposable absorbent article of claim 13 wherein the containment assembly further includes at least one front covering panel disposed between the lateral reinforcement member and the front end edge, the front covering panel covering at least a portion of the wearer's body which the front waist region is substantially adjacent when the absorbent article is worn.

16. The disposable absorbent article of claim 13 further including at least one supportive loop segment formed by at least a portion of the diagonal support member and at least a portion of the lateral reinforcement member and lying at least partially in the diagonal support zone of the wearer's body when the absorbent article is worn.

17. The disposable absorbent article of claim 13 wherein at least a portion of the absorbent core is disposed between the lateral reinforcement member and the front end edge.

18. A pre-closed disposable absorbent article for fitting about a wearer's body to contain excreta and/or bodily exudates, the wearer's body having a lower abdomen, hip joints, a small of the back, and a diagonal support zone lying across the small of the back over the hip joints and across the lower abdomen, the absorbent article comprising:
 a) a containment assembly having a longitudinal centerline, a lateral centerline, a front waist region, a back waist region opposed to the front waist region, a crotch region disposed between the front waist region and the back waist region, a front end edge, a back end edge, side edges, a topsheet, a backsheet, and an absorbent core disposed at least partially between the topsheet and the backsheet;
 b) at least one side panel in the back waist region extending laterally outwardly from the longitudinal centerline farther than the crotch region extends laterally at the lateral centerline and having a laterally extending edge forming a portion of the back end edge;
 c) at least one waist feature disposed substantially adjacent either the front end edge or the back end edge, at least a portion of the waist feature elastically extensible at least laterally; and
 d) at least one diagonal support member having a first end and a second end defining a major diagonal axis oriented nonparallel to the lateral centerline and nonparallel to the laterally extending edge of the at least one side panel when the absorbent article is in a flat uncontracted condition, the diagonal support member disposed such that when the absorbent article is worn the diagonal support member lies at least partially in the diagonal support zone of the wearer's body and closer to the lateral centerline than the nearer of the front end edge and the back end edge, the first end lying substantially adjacent the back waist region and the second end lying substantially adjacent the lower abdomen and closer to the lateral centerline than the first end.

19. The pre-closed disposable absorbent article of claim 18 wherein the containment assembly further includes at least one side covering panel disposed adjacent at least a portion of the diagonal support member, the side covering panel covering at least a portion of the wearer's body which the diagonal support member is substantially adjacent when the absorbent article is worn.

20. The pre-closed disposable absorbent article of claim 18 wherein the containment assembly further includes at least one front covering panel disposed in the front waist region, the front covering panel covering at least a portion of the wearer's body which the front waist region is substantially adjacent when the absorbent article is worn.

21. The pre-closed disposable absorbent article of claim 18 wherein at least a portion of the diagonal support member is elastically extensible at least in a direction substantially parallel to the major diagonal axis of the diagonal support member.

22. The pre-closed disposable absorbent article of claim 18 wherein the containment assembly has an inner surface having a coefficient of static friction to the wearer s body, the absorbent article further including at least one high friction retention zone disposed at least partially on the inner surface of the containment assembly in either the front waist region or the back waist region, the high friction retention zone having a coefficient of static friction to the wearer's body at least about twice the coefficient of static friction to the wearer's body of the inner surface of the containment assembly.

23. The pre-closed disposable absorbent article of claim 18 further including at least one fastening system, the fastening system disposed at least partially adjacent at least a portion of the side edges of the front waist region and/or the back waist region such that the fastening system substantially maintains the front waist region and the back waist region in a hoop configuration, the fastening system including refastenable fastening means.

24. The pre-closed disposable absorbent article of claim 18 further including at least one leg cuff, the diagonal support member and the leg cuff forming a substantially unitary structure.

25. The pre-closed disposable absorbent article of claim 18 wherein at least either the first end or the second end of the diagonal support member is unjoined to any other element of the absorbent article.

26. The pre-closed disposable absorbent article of claim 25 wherein the unjoined first end or second end of the diagonal support member has at least one diagonal support fastening system.

27. The pre-closed disposable absorbent article of claim 18 wherein the diagonal support member comprises two or more discrete elements, the discrete elements aligned substantially along the major diagonal axis of the diagonal support member such that the discrete elements function cooperatively to support the absorbent article substantially in the diagonal support zone of the wearer's body when the absorbent article is worn.

28. The pre-closed disposable absorbent article of claim 27 wherein the discrete elements of the diagonal support member have intermediate ends, at least one of the intermediate ends of at least one of the discrete elements having at least one diagonal support fastening system.

29. The pre-closed disposable absorbent article of claim 18 further including at least one permanent seam joining at least a portion of the opposing side edges at least in the front waist region and back waist region.

30. The pre-closed disposable absorbent article of claim 29 wherein the permanent seam substantially constitutes the diagonal support member.

31. The pre-closed disposable absorbent article of claim 18 wherein the containment assembly further includes at least one lateral reinforcement member having a first reinforcement member end and a second reinforcement member end, the lateral reinforcement member disposed between the front end edge and the lateral centerline of the containment assembly such that at least either the first reinforcement member end or the second reinforcement member end lies substantially adjacent the second end of the diagonal support member when the absorbent article is worn.

32. The pre-closed disposable absorbent article of claim 31 wherein the containment assembly further includes at least one front covering panel disposed between the lateral reinforcement member and the front end edge, the front covering panel covering at least a portion of the wearer's body which the front waist region is substantially adjacent when the absorbent article is worn.

33. A pre-closed disposable absorbent article for fitting about a wearer's body to contain excreta and/or bodily exudates, the wearer's body having a lower abdomen, hip joints, a small of the back, and a diagonal support zone lying across the small of the back over the hip joints and across the lower abdomen, the absorbent article comprising:

a) a containment assembly having a longitudinal centerline, a lateral centerline, a front waist region, a back waist region opposed to the front waist region, a crotch region disposed between the front waist region and the back waist region, a front end edge, a back end edge, side edges, a topsheet, a backsheet, and an absorbent core disposed at least partially between the topsheet and the backsheet;

b) at least one side panel in the back waist region extending laterally outwardly from the longitudinal centerline farther than the crotch region extends laterally at the lateral centerline and having a laterally extending edge forming a portion of the back end edge;

c) at least one waist feature disposed substantially adjacent either the front end edge or the back end edge, at least a portion of the waist feature elastically extensible at least laterally;

d) at least one diagonal support member having a first end and a second end defining a major diagonal axis oriented nonparallel to the lateral centerline and nonparallel to the laterally extending edge of the at least one side panel when the absorbent article is in a flat uncontracted condition, the diagonal support member disposed such that when the absorbent article is worn the diagonal support member lies at least partially in the diagonal support zone of the wearer's body and closer to the lateral centerline than the nearer of the front end edge and the back end edge, the first end lying substantially adjacent the back waist region and the second end lying substantially adjacent the lower abdomen and closer to the lateral centerline than the first end; at least a portion of the diagonal support member elastically extensible at least in a direction substantially parallel to the major diagonal axis;

e) at least one side covering panel disposed adjacent at least a portion of the diagonal support member, the side covering panel covering at least a portion of the wearer's body which the diagonal support member is substantially adjacent when the absorbent article is worn;

f) at least one lateral reinforcement member having a first reinforcement member end and a second reinforcement member end, the lateral reinforcement member disposed between the front end edge and the lateral centerline of the containment assembly such that at least either the first reinforcement member end or the second reinforcement member end lies substantially adjacent the second end of the diagonal support member when the absorbent article is worn, at least a portion of the lateral reinforcement member elastically extensible at least laterally; and g) at least one front covering panel disposed between the lateral reinforcement member and the front end edge, the front covering panel covering at least a portion of the wearer's body which the front waist region is substantially adjacent when the absorbent article is worn.

34. The pre-closed disposable absorbent article of claim 33 wherein at least a portion of the absorbent core is disposed between the lateral reinforcement member and the front end edge.

35. The pre-closed disposable absorbent article of claim 33 wherein the containment assembly has an inner surface having a coefficient of static friction to the wearer's body, the absorbent article further including at least one high friction retention zone disposed at least partially on the inner surface of the containment assembly in either the front waist region or the back waist region, the high friction retention zone having a coefficient of static friction to the wearer's body at least about twice the coefficient of static friction to the wearer's body of the inner surface of the containment assembly.

36. The pre-closed disposable absorbent article of claim 33 further including at least one fastening system, the fastening system disposed at least partially adjacent at least a portion of the side edges of the front waist region and/or the back waist region such that the fastening system substantially maintains the front waist region and the back waist region in a hoop configuration, the fastening system including refastenable fastening means.

37. The pre-closed disposable absorbent article of claim 33 further including at least one leg cuff, the diagonal support member and the leg cuff forming a substantially unitary structure.

38. The pre-closed disposable absorbent article of claim 33 wherein at least either the first end or the second end of the diagonal support member is unjoined to any other element of the absorbent article.

39. The pre-closed disposable absorbent article of claim 38 wherein the unjoined first end or second end of the diagonal support member has at least one diagonal support fastening system.

40. The pre-closed disposable absorbent article of claim 33 wherein the diagonal support member comprises two or more discrete elements, the discrete elements aligned substantially along the major diagonal axis of the diagonal support member such that the discrete elements function cooperatively to support the absorbent article substantially in the diagonal support zone of the wearer's body when the absorbent article is worn.

41. The pre-closed disposable absorbent article of claim 40 wherein the discrete elements of the diagonal support member have intermediate ends, at least one of the intermediate ends of at least one of the discrete elements having at least one diagonal support fastening system.

42. The pre-closed disposable absorbent article of claim 33 further including at least one permanent seam joining at least a portion of the opposing side edges at least in the front waist region and back waist region.

43. The pre-closed disposable absorbent article of claim 42 wherein the permanent seam substantially constitutes the diagonal support member.

* * * * *